United States Patent
Fabian et al.

(10) Patent No.: US 7,420,468 B2
(45) Date of Patent: Sep. 2, 2008

(54) SURGICAL IMPLEMENT DETECTOR

(76) Inventors: Carl E. Fabian, 5001 London Walk, Miami, FL (US) 33138; Frank O'Neill, 465 University Ave., Boulder, CO (US) 80302

( * ) Notice: Subject to any disclaimer, the term of this patent is extended or adjusted under 35 U.S.C. 154(b) by 276 days.

(21) Appl. No.: 11/299,106

(22) Filed: Dec. 9, 2005

(65) Prior Publication Data

US 2006/0187044 A1    Aug. 24, 2006

Related U.S. Application Data

(63) Continuation-in-part of application No. 11/055,348, filed on Feb. 10, 2005.

(51) Int. Cl.
*G08B 13/14* (2006.01)

(52) U.S. Cl. ............... 340/572.1; 340/572.4; 340/568.1

(58) Field of Classification Search ............. 340/572.1, 340/572.4, 573.1, 573.3, 573.4, 573.5, 571, 340/568.1, 593.13, 505, 10.1; 235/380, 384, 235/385

See application file for complete search history.

(56) References Cited

U.S. PATENT DOCUMENTS

| | | | |
|---|---|---|---|
| 5,057,095 A | 10/1991 | Fabian | |
| 5,105,829 A | 4/1992 | Fabian et al. | |
| 5,107,862 A | 4/1992 | Fabian et al. | |
| 5,188,126 A | 2/1993 | Fabian et al. | |
| 5,190,059 A | 3/1993 | Fabian et al. | |
| 5,329,944 A | 7/1994 | Fabian et al. | |
| 5,353,011 A * | 10/1994 | Wheeler et al. | 340/572.4 |
| 5,923,001 A | 7/1999 | Morris et al. | |
| 6,294,997 B1 * | 9/2001 | Paratore et al. | 340/572.1 |
| 6,992,587 B2 * | 1/2006 | Maeda et al. | 340/572.1 |
| 7,202,784 B1 * | 4/2007 | Herwig | 340/568.1 |
| 2003/0066537 A1 | 4/2003 | Fabian et al. | |
| 2005/0049563 A1 | 3/2005 | Fabian | |
| 2005/0049564 A1 | 3/2005 | Fabian | |

OTHER PUBLICATIONS

ATMEL Corporation, Read/Write Base Station U2270B, Datasheet, Dec. 2005, Atmel Corporation, San Jose, California, USA.
ATMEL Corporation, Data Communication via the TMEB8704 Serial Interface RS-232, Datasheet, Jan. 2006, Atmel Corporation, San Jose, California, USA.
ATMEL Corporation, TMEB8704 RFID Application Kit, Datasheet, Oct. 2005, Atmel Corporation, San Jose, California, USA.

* cited by examiner

*Primary Examiner*—Van T. Trieu

(57) ABSTRACT

Provided is a detector system for detecting a plurality of items each having at least one RFID tag attached thereto. The detector system may include a presence detector and/or a message detector. The presence detector may include a signal reader which receives modulated carrier frequencies from the RFID tags during a predetermined response time period for comparison to a reference level. The signal reader may be configured as a power integrator or a constellation discriminator. The power integrator sums the power contained in signals transmitted by the RFID tags by integration for comparison to an environmental noise level measurement taken during a quiet period. For the constellation discriminator, bits contained in the modulating message are compared to the bit pattern of a predetermined reference constellation. The detector system may be configured as a 3-state detector which combines the presence detector with a message detector that indicates the identification code of the RFID tags.

37 Claims, 27 Drawing Sheets

(Calibrate While Holding Signal Reader Away from Activation Regions)

(Self-Calibrate During Quiet Time, or Prior to Turn On)

| TAG DISPOSITION | RFID STANDARD READER | RFID WITH ANTI-COLLISION SYSTEM | RFID MULTI-TAG DETECTOR |
| --- | --- | --- | --- |
| 1 or more Tags at Extended Distances | (No Valid Signal) | (No Valid Signal) | ✓ |
| 2 or more Tags in Possible Contention | (No Valid Signal) | ✓ | ✓ |
| 2 or more Tags Within Range | (No Valid Signal) | ✓ | ✓ |
| 1 Tag Within Range | ✓ | ✓ | ✓ |
| 0 Tags Present | (No Tag Found) | (No Tag Found) | (No Tag Found) |

*Figure 18*

SURGICAL IMPLEMENT DETECTOR

CROSS-REFERENCE TO RELATED APPLICATIONS

The present application is a continuation-in-part application of U.S. application Ser. No. 11/055,348 entitled SURGICAL IMPLEMENT DETECTOR UTILIZING A RADIO FREQUENCY IDENTIFICATION MARKER filed on Feb. 10, 2005, which is related to U.S. application Ser. No. 11/054,844 entitled MULTIMODAL DETECTION OF SURGICAL SPONGES AND IMPLEMENTS filed on Feb. 10, 2005, the entire contents of all being expressly incorporated by reference herein.

STATEMENT RE: FEDERALLY SPONSORED RESEARCH/DEVELOPMENT (Not Applicable)

BACKGROUND

The present invention relates to radiofrequency identification (RFID) markers for detection of surgical implements and, more particularly, to an RFID marker embedded in or otherwise securely attached to a surgical implement such as a laparotomy pad or sponge, metallic surgical instrument or other implement and which is specifically adapted for preventing the inadvertent retention of such implement(s) during a surgical procedure.

Included in the prior art are many patents that disclose systems and methods for detection of surgical implements following surgery prior to wound closure. Such detection methods incorporate x-ray opaque markers within surgical implements and effect detection using postoperative x-ray of the patient or of discarded sponges. Also disclosed for detection of surgical implements are methods involving use of resonant tags made from magnetomechanical elements, capacitors, LRC oscillatory circuits and smart markers.

U.S. Pat. Nos. 4,114,601 and 4,193,405 to Abels disclose a medical and surgical implement detection system. Surgical implements such as metallic instruments, sponges, implantable devices and indwelling therapeutic devices and materials are detected within the human body or other area of interest by incorporating or adding a radiofrequency transponder. A microwave system mixes two fundamental microwaves having 4.5-5 GHZ frequencies and relies on a non-linear transponder to produce higher order product frequencies. The transponder may be a thin film of a ferrite material exhibiting gyro-magnetic resonance at selected frequencies or a solid-state device containing diodes and field effect transistors. A non-linear transponder signal is received by a receiving antenna and filtered to remove all fundamental microwave frequencies. Unfortunately, substantially all of the higher order microwave frequencies generated by the transponder are readily absorbed by the human body. Consequently, most of the higher order microwave frequency signals are lost before any non-linear transponder can be detected. In addition, the gyro-magnetic effect produces a relatively weak signal.

U.S. Pat. No. 4,658,818 to Miller, Jr., et al. discloses an apparatus for tagging and detecting surgical implements. A miniature battery-powered oscillator is attached to each surgical implement and activated prior to its initial use. The output of each oscillator has the form of a low powered pulse of 1-10 MHZ frequency, and is coupled to the body's fluids and tissue. Following surgery but prior to suturing, a detection system senses for any pulses generated by the oscillator within the body. The surgical implement detection system disclosed by the '818 patent is not passive. It requires a miniature battery, which is turned on at the beginning of the operation. When the operation is complete, the battery may have already discharged, in which event the surgical implement will not be detected by the apparatus.

U.S. Pat. No. 5,057,095 to Fabian discloses a surgical implement detector utilizing a resonant marker for use in human or animal tissue. The marker is triggered into resonance by the interrogating field. A resonance frequency signal emitted by the marker is detected by a separate detection circuit adjacent to the interrogating circuit. The marker resonates due to magnetostriction properties of an amorphous metal ribbon, a piezoelectric device or a tuned LRC circuit. The response from the marker constitutes a simple sine wave having a particular frequency, which is less than one gigahertz. A detector is responsive within an interrogation zone encompassing a surgical wound. The marker is adapted to undergo resonance solely at a pre-selected frequency below 1 GHz, causing a substantial change in its effective impedance. An electromagnetic dipole field is thereby generated, which produces an identifying signal identity. The interrogation means is also provided with a means for varying phase and/or direction of the interrogating field. A receiving means placed within the interrogation zone detects the "ring-down", phase-shift, impedance or other identifying characteristic of the element in resonance.

U.S. Pat. No. 5,188,126 to Fabian, et al. discloses a surgical implement detection system utilizing capacitive coupling for use in human or animal tissue. The system comprises a battery-powered marker, which is secured to the surgical implement and positioned within a surgical wound. A detection means has an antenna disposed in close proximity of the tissue. Means are provided for capacitance coupling of the marker with the antenna and activation of the battery-powered marker. A field generating means associated with the detection system generates an electromagnetic field having a predetermined frequency band ranging from about 10 MHz to 1 GHz. The electromagnetic field causes the marker to produce a signal in the form of a sinusoidal wave having unique signal identity. A battery powers the capacitive marker, which will not function when the battery is discharged. Inasmuch as there is no means to verify the status of the battery, this method for detection of surgical implements is vulnerable to battery failure.

U.S. Pat. No. 5,190,059 to Fabian, et al. discloses a surgical implement detector utilizing a powered marker for use in human or animal tissue. A battery-powered marker is secured to a surgical implement positioned within the wound. An electromagnetic field generating structure in the battery-powered marker is provided for generating within the transmitting zone an electromagnetic field having a predetermined frequency band, providing the marker with signal identity. The response from the battery-powered marker is a simple sine wave having a particular frequency. Such a response does not comprise a digital code as it lacks the capacity for identifying a surgical implement. Battery power is required such that detection is not effected when the battery is discharged.

U.S. Pat. No. 5,541,604 to Meier discloses transponders, interrogators, systems and methods for elimination of interrogator synchronization requirement. A Radiofrequency Identification (RFID) system has an interrogator and a transponder, the interrogator having a first tuned circuit of a powering frequency for sending a powering burst to a transponder, a filter/demodulator for receiving a wireless, modulated RF response from a transponder. The interrogator additionally has a second tuned circuit in electrical communication with a modulator. The second tuned circuit has a selected bandwidth about a communication frequency. The selected bandwidth does not substantially overlap the powering frequency and encompasses the bandwidth of the modulated carrier of the RF response. The carrier is modulated using pulse width modulation (PWM), pulse position modulation (PPM), frequency-shift keying modulation (FSK), or another type of modulation methods. The interrogator also has a controller in electrical communication with the filter/demodulator and the tuned circuits. It enables the first tuned circuit to send the powering burst during a first time period and enables the modulator in electrical communication with the second tuned circuit to receive the RF response during a second time period. The transponder has a tuned circuit. A tuning circuit in electrical communication with the tuned circuit modifies the frequency characteristics of the tuned circuit. The circuit is thereby tuned during the powering burst to the powering frequency. It is also tuned during the RF response to the communication frequency. The transponder also includes a demodulator in electrical communication with the tuned circuit for receiving the RF interrogation therefrom and for demodulating data from the RF interrogation. This current generation RFID device sends a preset code to the interrogator. It is powered entirely by the power burst signal provided in the first time period and is capable of transmitting the code at a high rate to the interrogator.

U.S. Pat. No. 5,664,582 to Szymaitis discloses a method for detecting, distinguishing and counting objects. A marker made from a nonmagnetostrictive strip of amorphous or crystalline material produces higher harmonic excitations when energized by an alternating magnetic field. The higher harmonics are detected by the exciting antenna. This passive, non battery-powered device receives a fixed second harmonic frequency sinusoidal signal based on the size, shape and material of the marker. Information is not digitally encoded and therefore the marker has no means for identifying individual counting objects.

U.S. Pat. No. 5,931,824 to Stewart, et al. discloses an identification and accountability system for surgical sponges and includes machine-readable information located on a plurality of surgical sponges used in the surgical procedure. At the end of an operation the surgical implements are machine read to determine whether any of the sponges are missing. The system also includes an x-ray detector for the detection of missing sponges. Detection of sponges placed within a surgical wound is not effected unless the absence of a sponge is detected during the sponge count procedure following surgery. Actual location of a missing sponge requires x-ray examination.

U.S. Pat. No. 6,026,818 to Blair, et al. discloses a tag and detection device. An inexpensive tag has the form of a ferrite bead with a coil and a capacitor, or a tag of flexible thread composed of a single loop wire and capacitor element. The detection device locates the tag by pulsed emission of a wide band transmission signal. The tag resonates with a radiated signal, in response to the wide band transmission. Resonation occurs at the tag's own single, non-predetermined frequency, within the wide band range. The pulsing action of the wide band transmission builds the non-predetermined, radiated signal intensity over the ambient noise levels. This radiated signal is a sinusoidal wave of non-predetermined frequency and does not have digital information that identifies a particular sponge or surgical pad.

U.S. Pat. No. 6,076,007 to England, et al. discloses surgical devices and their location. A surgical device, such as a catheter or a prosthesis, carries, at a predetermined location, a tag composed of a high permeability, low coercivity magnetic material having a magnetized bias element. The tag is interrogated with a rotating magnetic field. Interaction between the tag and the rotating magnetic field is detected by a flying null system to determine the location of the tag within the human or animal body. Typically, the marker will be in the form of a thin film, a wire or a strip. The response signal from the tag is a sinusoidal wave with no digital information. The detection system is based on flying null technology. The tag is used for locating a catheter tip, not a sponge or surgical pad within a surgical wound.

U.S. Pat. No. 6,424,262 and U.S. patent application No. 20040201479 to Garber, et al. disclose applications for radiofrequency identification systems. An RFID target is used, together with magnetic security element and a bar code reader, to check out and manage library materials such as reference books, periodicals, and magnetic and optical media. This disclosure has nothing to do with detecting sponges or surgical pads in a surgical wound.

U.S. Pat. No. 6,838,990 to Dimmer discloses a system for an excitation leadless miniature marker. An excitation field excites a leadless marker assembly. The system comprises a source generator assembly having a power supply, an energy storage device, a switching network and an untuned source coil interconnected and configured to deliver a selected magnetic excitation signal waveform, such as continuous bipolar or unipolar waveform, or a pulsed magnetic excitation signal waveform. The power supply is configured to deliver power to energize the energy storage device. The switching network is configured to: direct electrical current through the source coil. It alternately switches between a first on position and a second on position. Stored energy is alternately transferred from the energy storage device to the source coil and from the source coil back to the energy storage device. The source coil is coupled to the switching network to generate an excitation signal. Untuned excitation is used by the source coil to look for resonance from a set of markers embedded in human tissue. Information is processed using an array sensor to three-dimensionally locate a given marker. This system does not locate sponges or surgical pads misplaced in a surgical cavity. The frequency response of a target is sinusoidal and has no digital capability.

U.S. patent application No. 2002/0143320 to Levin discloses tracking medical products with integrated circuits. Radiofrequency identification devices comprising a microprocessor, memory, analog front end and antenna are used to communicate with a remote unit. The remote unit has a processor memory and transreceiver that receives digital data from radiofrequency identification devices attached to medical products, such as a pharmaceutical product, a blood product or a tissue product. The radiofrequency identification device is first scanned and then rescanned at the end of the surgical procedure. There is no indication that the radiofrequency identification devices are encapsulated. Neither is there any indication that the RFID devices are incorporated in a sponge, surgical pad or surgical implement. Further, there is no indication in the Levin application that the RFID devices are scanned during surgery to establish the location of the sponge or surgical pad. There is also no indication in Levin application that the RFID devices are scanned at the end of an operating procedure to establish that no sponges or surgical pads are left behind in a surgical cavity.

U.S. patent application No. 2003/0006878 to Chung discloses a smart tag data encoding method. Information is stored in a smart tag having a memory. The smart tag has two memory portions. One of the partitions is permanent and cannot be erased. A second memory portion stores application specific data. The second memory portion also stores a relational check number, which validates the integrity of the data stored in the second memory, thereby detecting memory alteration or corruption. This smart tag data encoding method has nothing to do with detecting a sponge or surgical pad left behind in a surgical wound.

U.S. patent application No. 2003/0057279 to Uozumi et al. discloses an identifying system for an overlapped tag. An RFID and one or more resonance capacitors connected through on-off switches may be turned on or off by a remote control circuit. The overlapping tags may be interrogated using an RFID system, or one more resonance capacitors. The Uozumi et al. system does not detect sponges and surgical pads in a surgical wound, since they are not expected to overlap. Signals from the resonant capacitors of Uozumi et al. form a sine wave comprising electromagnetic radiation and do not carry a digital code U.S. patent application No. 20030066537 to Fabian, et al. discloses a surgical implement detection system. Surgical implements used during an operating procedure are detected in human tissue. Markers attached to the surgical implements change their impedance at a preselected frequency in the presence of an electromagnetic field. The system uses a magnetomechanical element which vibrates at a preselected frequency when excited. This preselected frequency, when detected, indicates the presence of a surgical implement to which the magnetomechanical marker element is attached. The marker resonates only at a fixed frequency and provides no digital information suited for identifying a sponge or a surgical pad.

U.S. patent application No. 20030105394 to Fabian, et al. discloses a portable surgical implement detector. Surgical implements used during an operating procedure are detected in human or animal tissue. Markers attached to the surgical implements change their impedance at a preselected frequency in the presence of an electromagnetic field. Each of the markers is thereby provided with signal-identifying characteristics. The portable detector sweeps the surgical cavity with a range of frequencies which excites and vibrates markers attached to surgical implements at preselected frequencies, causing their detection. The markers resonate at preselected frequencies in the form of sinusoidal waves, but do not provide digital data suited for identifying a sponge or surgical pad.

U.S. patent application No. 20030192722 to Ballard discloses a system and method of tracking surgical sponges. The sponges have a radiopaque object embedded therein which is visible when the sponges are x-rayed. All sponges removed from the surgical wound are placed into a sponge container which is provided with an internal device to x-ray and identify the sponges after use. However, because the sponges are not x-rayed when first put into use and because it is not possible to x-ray the sponges when they are in the patient wound, the Ballard system is incapable of determining whether all sponges have been removed from the patient wound or whether any sponges have been left behind in the patient wound.

U.S. patent application No. 20040129279 to Fabian, et al. discloses a miniature magnetomechanical tag for detecting surgical sponges and implements. This tag is a magnetomechanical device and is excited by the interrogating magnetic field. The interrogating field is switched off, and the ring down characteristic of the resonant target is detected. The system does not provide digital means for identifying a sponge or surgical pad.

U.S. patent application No. 20040250819 to Blair, et al discloses an apparatus and method for detecting objects using tags and a wideband detection device. An apparatus and method for the detection of objects in the work area, such as surgical sites, including a detection tag affixed to objects used during surgery, is disclosed. The apparatus and method feature interrogates with a transmitter emitting a pulsed wideband signal, prompting the tag element to provide a return signal, which is received and analyzed. The device features an antenna portion containing a single or a plural ring-shaped antenna. Also, the pulsed wideband interrogation signal may be pulsed-width modulated or voltage-modulated. The pulsed signals trigger a continuing response signal from the tag in its response frequency range, which increases in intensity to the point where it becomes differentiable from background noise and is detected within the wideband range by the signal detector as an indication of the presence of the tag. The tag is excited by a wide band pulsed interrogation signal, which builds up the output of the tag and can be detected over ambient electronic noise. The tag signal has a predetermined frequency in the form of a sinusoidal wave, and does not carry digital information suitable for identifying laparotomy pads or sponges retained within the wound cavity.

U.S. patent application No. 2005/0003757 to Anderson discloses an electromagnetic tracking system and method having a single-coil transmitter. The system includes a single coil transmitter emitting a signal, a receiver receiving a signal from the single coil transmitter, and electronics for processing the signal received by the receiver. The electronics determine a position of the single coil transmitter. The transmitter may be a wireless or wired transmitter. The receiver may be a printed circuit board. The electronics determine position, orientation, and/or gain of the transmitter. The single coil transmitter is a powered device and may be wired or wireless. It is not a passive device that can be incorporated in a sponge or surgical pad due to the requirement for a reliable power source.

PCT patent application No. WO 98/30166 to Fabian et al. discloses a surgical implement detector utilizing a smart marker. The surgical implement is appointed for disposition within human or animal tissue and is made to be electronically identifiable by affixing thereto a smart marker, which is an unpowered integrated circuit with EEPROM memory carrying a code. When the smart marker is sufficiently close to the reader antenna, a voltage is generated within the marker antenna that charges the capacitor and powers the integrated circuit. A switch is opened and closed to transmit the stored code in the EEPROM memory, providing identification and recognition of a smart target attached to a surgical sponge. The marker antenna operates at a frequency of near 125 KHz. The frequency of information transfer to the reader is very slow, due to the switching on and off action.

Despite the above noted deficiencies associated with RFID devices, certain industries have successfully implemented such technology for various purposes. For example, RFID technology has been successfully used to track cattle by the placement of RFID tags on cattle ears. The RFID tags may be read automatically or manually by a hand-held scanner in order to identify individual cattle. The cattle's identity may be linked to a computer database allowing access to a large amount of detailed information regarding the animal's origin, breeding, age and weight. Furthermore, such RFID tags may be utilized to identify the proximity of certain cattle to a feeding trough. Such RFID tags can be active, passive, or semi-active. Unfortunately, RFID systems such as those used in cattle tracking suffer from several critical deficiencies that detract from their overall utility. For example, RFID systems designed for cattle identification are understood to be limited to a range of just a few inches. Unfortunately, in surgical applications, a greater range is required. More specifically, in surgical applications, a range of at least 8 inches or more is required in order to adequately scan a patient's wound from above and reliably detect the presence of an RFID tag to which a surgical device may be attached.

Another deficiency of prior art RFID systems is that they are optimized to identify one or more RFID tags which are harmless to the environment being interrogated such as in a cattle yard, on a warehouse pallet, or in toll booth lane. In this regard, the primary goal of most RFID systems of the prior art is to successfully collect an identification message from the RFID tag. Detecting the mere presence of an RFID tag is typically of secondary importance.

However, in the surgical environment, these priorities are reversed. More specifically, in a surgical environment, it is of primary importance to detect the presence of all RFID tags such that the items to which they are attached may be removed from the patient wound. It is of secondary importance to identify the RFID tag. As such, the unique priorities of surgery means that the application of RFID detection systems for the surgical environment may involve non-obvious methodologies and system configurations.

Although at higher frequencies, (typically 13.56 MHz, 850 to 950 MHz, or 2.45 GHz), the added bandwidth permits the processing of multiple RFID tags at one time, RFID systems that operate in the low frequency ranges such as at 125 kHz typically allow for the stimulation of only one nearby RFID tag at a time. Once the RFID tag is stimulated, a signal reader may then retrieve a digital ID code impressed upon the signal. Unfortunately, the presence of two or more RFID tags within range of the detector generally results in a failure to acquire identification codes from any of the RFID tags due to "data collision" between the RFID tags. In this regard, current RFID readers are generally incapable of determining the presence of multiple RFID tags within a scanned area or of determining the identification code of any one of the RFID tags in an area containing multiple RFID tags.

The above-mentioned deficiencies of current RFID readers could unfortunately mean that either two or more RFID tags are present in the area, or, that there are no RFID tags present in the area being scanned. As such, there is currently no reliable method using conventional RFID tagging technology to verify whether or not surgical items are present after the end of an operation (i.e., prior to wound close) absent the incorporation of more expensive collision-control RFID tag technology. The failure to adequately identify and remove such items prior to wound closure is fairly widespread and well-documented in medical literature. Unfortunately, inadvertent retention of surgical items in the patient can result in serious complications for the patient and even death.

Another deficiency of prior art RFID systems is that the range of RFID tag detection is dependent upon the degree to which the RFID reader and the RFID tag are aligned with one another. When the antenna coils of the RFID tag and the RFID reader are aligned for best energy coupling, detection range is as much as 50-100% greater than when the antenna coils are oriented at 90° relative to one another. Unfortunately, there is no way to determine the orientation of the RFID tag which may be hidden from view in the patient wound. Therefore, detecting a tagged surgical item may be unsuccessful if the RFID reader antenna is not optimally-oriented with respect to the unseen RFID tag.

As so noted, the ability to detect an RFID tag may be compromised due to misalignment between the RFID tag antenna and the remote detector unit antenna. The occurrence of this event has been very low (less than 5 percent) and does not occur when individual readings are obtained. Nonetheless, to counteract the possibility of misalignment, the installation of two or more RFID tags on the same surgical implement may eliminate this event. Unfortunately, the installation of multiple RFID tags on the same surgical implement will result in data collision between the RFID tags and therefore requires that anti-collision measures be taken.

One solution to the above-mentioned problem is the incorporation of anti-collision technology. More specifically, with anti-collision technology, an identification code may be retrieved from two or more RFID tags in a scanned area during simultaneous interrogation of multiple RFID tags. Such anti-collision technology operates by delaying the response of each RFID tag by an appropriate amount of time in order to avoid simultaneous responses at the signal reader which, in turn, avoids corruption of signal data from the RFID tags. Unfortunately, this delay in RFID tag response increases the power requirements for each RFID tag. In a passive system, a limited amount of power is typically collected from the signal transmitted by the RFID reader (i.e., interrogator) such that a battery may be additionally required to provide power for the extended duration due to signal delay.

In addition to the added power requirements, a further deficiency associated with anti-collision technology is that such systems are typically more costly than RFID tag systems that operate on a one-at-a-time basis because they require the tags to have read/write capability. The increased cost of anti-collision technology in the RFID detection system may be prohibitive when the instrument or implement to which an RFID tag is attached is less expensive than the RFID tag itself.

As can be seen, there remains a need in the art for a highly reliable, surgical implement detection system wherein RFID tags may be attached to laparotomy pads or sponges and other non-metallic items as well as metallic instruments or implements for detection thereof. Preferaby the surgical implement detection RFID tag is passively powered (i.e., non-battery powered). Also needed is a marker of the type described above which can withstand cleaning and sterilization procedures commonly employed, and resists exposure to body fluids such as blood or saline solutions. Additionally, a surgical implement marker and corresponding detection device, is needed to provide a reliable indication of the location of foreign objects within a surgical wound during and at the completion of a surgical procedure prior to wound closure.

Furthermore, there exists a need in the art for a reliable detector system that utilizes RFID technology and which is specifically configured to provide an indication about the presence of multiple RFID tags in a specific area such as within a surgery wound. More specifically, there exists a need in the art for an RFID detector system that is capable of indicating whether one or more RFID tags are present within a given range or, alternatively, whether no RFID tags are present within the range. Even more specifically, there exists a need in the art for an RFID detector system that accurately and reliably detects the mere presence of one or more RFID tags within a surgical wound and preferably at a range of at least 8 inches with at least a 95 percent probability of an accurate determination of presence or non-presence.

Also, there exists a need in the art for an RFID detector system that allows for an indication of the surgical implement or instrument (i.e., via the identification code of the RFID tag) once located such that the surgical item can be inventoried. Additionally, there exists a need in the art for an RFID detector system that preferably operates at a relatively low frequency such as at 125-134 kHz in order to minimize the detrimental effects encountered in the upper frequencies, including increased signal attenuation by body tissue and nearby metallic objects. In addition to these disadvantages encountered in the upper frequency range, further drawbacks are encountered as the Gigahertz range is approached. As is well known in the art, microwave ovens typically operate at this frequency to heat watery foods and can therefore potentially cause unwanted localized heating (i.e., cooking) of body tissue by inducing rapid vibration of water molecules contained therewithin. The low frequency range, on the other hand, is not only less affected by intervening tissue and metal, but has the added benefit of avoiding issue heating. Lastly, there exists a need in the art for an RFID detector system that is of low cost such that the detector system is feasible for implementation in hospitals having large quantities of surgical items and implements.

BRIEF SUMMARY

The present invention is a surgical implement detector consisting of radiofrequency identification (RFID) marker and a detection unit. This RFID tag or marker may be a passively-powered device with a read-only memory of burned-in digital code or a user programmable memory. It may not necessarily rely on battery power although active powering of the RFID tags may be a suitable option depending on desired performance parameters. The surgical implement detector is highly reliable in operation and capable of detecting various surgical implements such as metallic and non-metallic instruments including surgical sponges, gauze pads, and other items to which the radiofrequency marker is attached. The RFID marker can be very small in size and is typically encapsulated in glass or inert polymer making it able to withstand cleaning and sterilization operations. It is not adversely affected by blood or saline solution present in a surgical wound.

This small RFID marker has an antenna which couples with the interrogating antenna of the detection unit. A power burst from the interrogating antenna charges a capacitor located within the RFID marker. The charged capacitor then powers the logic and processing functions of an integrated chip, which reads a burned-in code present in the read-only memory thereof or the code in its user programmable memory. A carrier frequency is used for communication between the RFID marker and the interrogating antenna of the detector.

This carrier frequency is modulated by the RFID marker using pulse width modulation (PWM), pulse position modulation (PPM), frequency-shift keying modulation (FSK), or another modulation method to represent and communicate the coded numeric value. The interrogating antenna receives the modulated electromagnetic carrier wave and decodes, detecting the code communicated by the RFID marker. This numeric code identifies a tag-bearing surgical implement, which may be a surgical sponge, gauze pad, metallic instrument, or other item and is kept track of remotely during and after a surgical procedure permitting an inventory of all such items and preventing such items from accidentally being left behind when the wound is closed.

RFID tags generally operate at frequencies ranging from 30 kHz to 2.45 GHz. As used herein, the term "low frequency" will generally refer to the frequency band of between 125-134 kHz. The term "high frequency" will refer to the frequency band operating around 13.56 MHz and the term "ultra-high frequency" will refer to the frequency band of between 850-950 MHz. As was indicated above, RFID tags may also operate in the Gigahertz range of approximately 2.45 GHz with special uses. For applications to which the present invention is directed, namely, the identification of implements used at surgery, RFID tags as used herein will be considered in two broad categories: "low frequency" will refer to the same "low frequency" range cited above (i.e., 125-134 kHz) and the term "upper frequency" range will encompass both the "high frequency" (i.e., 13.56 MHz) and the "ultra-high frequency" (i.e., 850-950 MHz) ranges cited above.

Low frequency RFID tags (typically operating at about 125 kHz) can be very tiny in size, are relatively inexpensive to manufacture, and their detection is moderately resistant to shielding by adjacent metal or attenuation by intervening tissue. Glass enclosure makes them robust enough to undergo sterilization procedures an indefinite number of times. Although small and relatively simple members of the RFID family, the low frequency RFID tags can still carry enough coded data to provide separate identity to many millions of RFID tags, enough for every surgical item in a large hospital. However, due to bandwidth constraints, their low carrier frequency range limits their RFID functionality and systems based on these RFID tags generally operate reliably only when a single tag is present within the interrogation zone at a time. This aspect prevents bulk identification and requires that each RFID tag must be read individually, one-at-a-time.

This latter aspect may be regarded as a disadvantage in some operating rooms where it may be desired to identify multiple tags rapidly and simultaneously and therefore is preferable to use RFID tags that operate in the upper frequency range. On the other hand, reading of each tagged item individually would obviate the concern that n RFID tag may escape detection because of shielding or being out of detection range.

At the upper frequencies, (e.g., 13.56 MHz, and 850 to 950 MHz), the added bandwidth permits the development of systems which can reliably process multiple tags in the interrogation zone within a short period of time. This would allow a number of implements to be identified and inventoried simultaneously, such as all the items on the instrument table or all the implements within the wound cavity. However, the upper frequency markers tend to be relatively bulky, may be more expensive to manufacture, and their detection is more susceptible to attenuation by intervening body tissue and shielding by adjacent metallic objects.

Since each system has advantages and disadvantages, the ultimate choice of which type of RFID tag to utilize in a given surgical department will no doubt vary from one department to another and will be individually made by the personnel of each institution. Generally stated, the invention involves the use of one or more RFID tag or markers in all frequency ranges, embedded in or otherwise securely attached to a surgical implement of some description, whether a surgical sponge, gauze pad, metallic surgical instrument or other object.

The metal present in a surgical instrument may interfere with the electromagnetic communication between the RFID marker and the interrogating antenna, a phenomenon referred to herein as "shielding". For this reason, a non-metallic extension may be used to attach the RFID marker to a metallic instrument, displacing the marker from the metallic object and thereby enhancing the communication between the marker and detector and minimizing the chance of shielding.

Surgical sponges and gauze pads are used for a number of purposes during an operation, including absorption of blood and fluids from a surgical cavity, maintenance of structures in position, and other uses. Although almost any surgical implement may be inadvertently left behind in a surgical cavity and closed into the wound, the item by far most commonly left behind is the surgical sponge and when retained, this item can result in dire complications, including infection, abscess, fistulization, obstruction and even death. The medical literature is replete with such reports.

The present invention overcomes this problem by securing RFID tags or markers to the various implements used in surgery, whether surgical sponges, gauze pads, or metallic instruments. When attached to a metallic instrument, a non-metallic extension can be utilized to decrease the chance of shielding. An implement thus equipped with such an RFID marker can be readily identified by a stationary scanner mounted upon a rollaway cart or by an accompanying hand-held scanner. A receiving unit detects a RFID signal emitted by the marker. The signal represents a particular code which allows immediate identification of any so-marked surgical implements remaining within the surgical cavity before closure of the surgical incision. Advantageously, with the present invention the retention of surgical sponges, the soft, absorbent, cotton cloths, 14 or 18 inches square, the item most commonly left behind and the item most likely to cause serious complications when retained, can be virtually eliminated.

This RFID marker includes a miniature integrated electronic circuit connected to an antenna, which is typically a copper wire wound over a ferrite core. A capacitor circuit acts as a power source when charged by the electromagnetic radiation power burst emitted by an interrogating antenna of a detecting remote unit. The antenna of the RFID marker first couples with the interrogating antenna of the detecting remote unit, which may be a hand-held scanner or a fixed scanner situated adjacent to the operating table. An incoming burst of electromagnetic radiation is used to charge the capacitor. Upon being charged, the capacitor provides power to the integrated circuit, which reads a digital code that is permanently burned in the memory of the integrated circuit, and synthesizes a broadcast signal which modulates the carrier signal using pulse width modulation, pulse position modulation or frequency shift keying modulation. Digital data of the code is transmitted to the hand-held antenna or to the fixed remote antenna using the same detection unit. Since the digital code representing a given surgical implement cannot be generated by other than the particular RFID device implanted, detection is highly specific and there is no room for error. The RFID tag or marker is encased in a glass envelope so that the implement to which it is secured can be laundered, sterilized and packaged for single or multiple use.

RFID markers are of more recent development than the older magnetomechanical resonant tags over which they have the following important advantages. They can be made much smaller, (11 mm by 2.5 mm—as small as a grain of rice), carry coded identifying data, and when enclosed in glass or polymer are sufficiently robust in construction to allow repeated sterilization by virtually any method currently in use—heat, gas, chemical, or gamma radiation. Depending on the carrier frequency used and the type of construction, they can vary significantly in characteristics, including size and cost, the distance over which they can be read, the degree of signal attenuation resulting from shielding and intervening tissue, the amount of coded data contained, and whether multiple tags can be read at once within an interrogation zone or whether each tag must be read separately.

Since these RFID tags can have many different attributes, the selection of the type of RFID tag to utilize in a given surgical department may vary. The low frequency range tags may be selected because of their small size and lower cost, and relative resistance to tissue attenuation and shielding, even with the knowledge that these tags must be read individually. A factor which compensates for this disadvantage is that when the tags must be read individually with a close, handheld reader such RFID tags cannot escape detection because of shielding or being out of range and assures that every tag is detected and read, Utilization of the upper frequency tags with their higher bandwidths will allow multiple tags, such as all the tagged implements on the instrument table, to be processed in the interrogation zone in a short period of time, and will permit tagged implements items to be read while still within the patient, providing shielding is prevented by use of a non-metallic spacer to secure the RFID tag to the metal implement, as noted above. Since, as noted, each type RFID marker has advantages and disadvantages, the choice of which type of RFID marker to employ may be made on a case-by-case basis.

In use, a surgeon or nurse scans each of the RFID-tagged surgical implements or instruments as they are introduced into the operative field and again upon the conclusion of surgery, just prior to wound closure, to verify that no surgical implements have been left behind. Each RFID tag has its own code, permitting an electronic inventory of all so tagged items employed during the operation. Scanning with this system, utilizing either the remote fixed antenna or the hand-held scanning antenna should be highly accurate. The resulting electronic inventory of all tagged surgical implements employed during surgery will mean that no items will be unaccounted for and left behind and has the added benefit of allowing the hospital to create a charge for items used.

As was earlier mentioned, RFID systems require "anti-collision technology" in order to reliably detect multiple tags. Under prevailing technology, when more than one tag is present, each having distinct identification codes, the presence of more than one code can interfere (i.e., collide) with the identification of either unless some means is provided to keep their identifications apart from one another. This adds complexity and expense to these tags. Low frequency systems of the prior art now indicate only one of only two possible responses: either "tag found" or "tag found along with its identification code". If more than one tag is present, the reader, being unable to identify more than one at a time, will give the indication "no tag found".

A modification is herein made to the existing RFID technology. The change to the technology claimed herein may provide two different responses: "no tag found", and "more than one tag present" without giving specific identification data of any RFID tag or item to which it may be attached. This will obviate the need for anti-collision means to be incorporated in each tag and allow the patient to be scanned at the conclusion of surgery simply to verify that no tags remain within the wound. If any tags are noted to be left in the wound, they will be removed by the surgeon at which time they can be specifically identified by a hand-held reader, one-at-a-time.

Also claimed herein is a modification to RFID technology for surgical implement detection in a wound wherein the detector system is specifically configured to combine a presence detector with a message detector in order to allow for the display of data relating to the existence of at least one of the following three states: "non-presence of RFID tags", "presence of one or more RFID tags" and "identification code of one of the RFID tags", in a so called "3-state" detector system. The 3-state detector system may operate via a procedure wherein detection of the presence of at least one of the RFID tags is followed by detection of the identification code of at least one of the RFID tags. In an "alternating" procedure, detection of the presence of multiple RFID tags occurs in alternating manner to the detection of the identification codes of the RFID tags and is preferably conducted in a manner so as to minimize movement of tissue within the patient wound in order to avoid bleeding and/or other damage or complications.

The implementation of the above-mentioned RFID technology avoids the more complex and significantly more expensive anti-collision technology that is required for multiple tags which requires a read/write sequence in order to accurately and reliably detect and identify multiple RFID tags that are within detection range (i.e., activation region) of a remote detector. Furthermore, the ability to detect multiple RFID tags within a patient wound is accomplished in the detector system using simple, elegant and low cost analog architecture which utilizes squelch circuitry and power detection as opposed to more common digital solutions which utilize various techniques including cyclic-redundancy-check (CRC), message headers and other methods for detecting bit errors in received signal.

More specifically, the analog architecture is implemented in a signal reader (i.e., a receiver portion of a remote detector unit) that receives signals from the RFID tags during a pre-determined response time period and then compares the signal to a reference level established during a quiet period in order to determine the presence of RFID tags. The detector system may incorporate a power integrator in the remote detector unit and which sums power contained in a composite signal received at the remote detector unit. The composite signal may be comprised of at least one of the following two sources: (1) signals transmitted by at least one of the RFID tags within the patient wound, or, (2) signals transmitted by a combination of environmental noise and at least one of the RFID tags. The power is summed by integration and is then compared to the environmental noise level in order to determine the existence of RFID tags.

Alternatively, the signal reader may be configured as a constellation discriminator that receives bits contained within the signals of the multiple RFID tags. The bits may be comprised of one of the following: (1) uncorrupted bits transmitted by at least one of the RFID tags, or, (2) corrupted bits transmitted by a combination of environmental noise and at least one of the RFID tags. The constellation discriminator may include a comparator which is operative to receive bits contained in the signals from the RFID tags during the pre-determined response time period and compare a pattern of the bits to a predetermined reference constellation. The reference constellation is a measurement of the bit pattern of environmental noise which is measured during a quiet period. The constellation discriminator is specifically configured to allow the detector system to indicate the presence of RFID tags when the bit pattern is sufficiently distinguished from the reference constellation.

The detector system as described herein applies to semi-conductor based RFID tag systems of both passive and active varieties and may further be configured to operate across all frequency bands including the intermediate frequencies. However, as was earlier mentioned, the low frequency bands may be most desirable for surgery applications. Depending upon the signal-to-noise ratio (SNR), the range with which RFID tags may be reliably detected is likely to increase relative to prior art systems. For example, in half duplex (HDX) operation of the detector system, range may be expected to increase by approximately two times assuming a 6 dB SNR setting relative to the environmental noise. Even further, a range within which the detector system may reliably (e.g., 95 percent reliability) detect multiple RFID tags within the patient wound may be expected to increase up to almost three times that of prior art systems depending upon the modulation method applied. Therefore, a standard range of 4 inches for RFID detection systems of the prior art may be translated into a range of from about 6 to 12 inches given the enhancements claimed herein and described in detail below.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 8b is a graph of signal power versus time and illustrating a positive indication of the presence of the RFID tag when power contained within the RFID signal is greater than an environmental noise level measurement taken during a predetermined response time period;

FIG. 18 is a table illustrating the effectiveness of the detector system of the present invention in comparison to prior art detector systems which can be made to detect multiple RFID tags using "anti-collision" technology.

DETAILED DESCRIPTION

Figure 1:
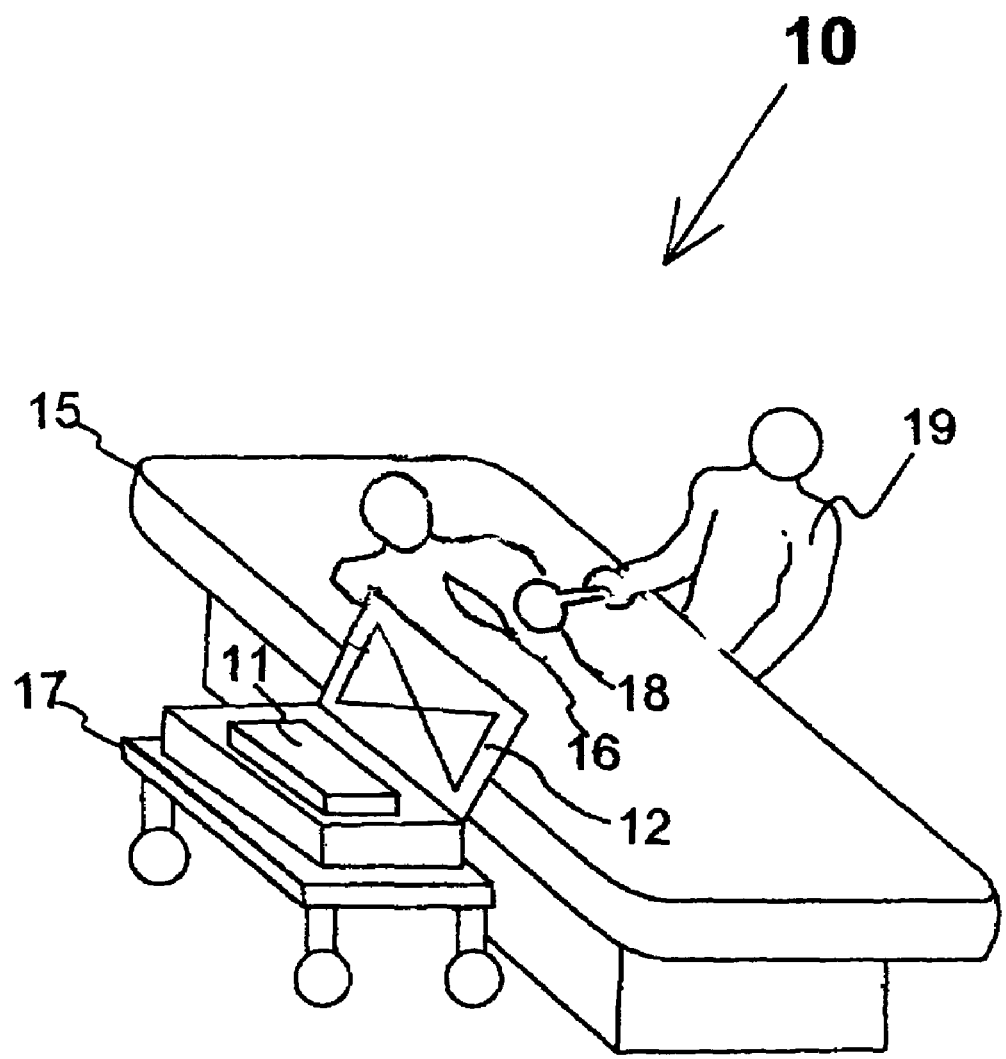
FIG. 1 is a schematic diagram showing an operation in progress in which a radiofrequency identification (RFID) and detection system is in use.

This invention relates to a surgical implement detector or detector system utilizing a radiofrequency identification (RFID) tag or marker which is secured to a surgical implement, whether a surgical sponge, gauze pad, metallic instrument or other item, and is detected by an antenna attached to either a remote, fixed scanner or by a hand-held scanner. Each RFID-tagged item is read by the RFID reading device upon introduction into the operative field, before insertion into the wound and again upon conclusion of surgery, and a record is made thereof. If the upper frequency tag is used, the scanner can also be used to locate the RFID-tagged items within the patient at any time during surgery.

If the low frequency RFID tag is used, the reader individually identifies each RFID tag upon introduction into the operative field and records it on a list and again identifies and records each tagged item upon removal from the operative field and both inventory lists are matched. When the low frequency RFID tag is used, requiring each tag to be read individually, shielding is not of concern. Even when the tag is affixed directly to a large metal implement such as a retractor, an individual reading can be easily obtained with the hand-held reader. More specifically, the RFID tag then is used to identify the various surgical implements being utilized and more importantly, to verify that no tagged items are left behind in a surgical cavity when the wound is closed.

The RFID tag or marker is an integrated circuit with a burned-in digital code in a read-only or user programmable memory. It is powered by a capacitor circuit that is connected to an antenna, which typically comprises a ferrite element wound with copper wire. When the RFID tag or marker is in the presence of electromagnetic radiation, the antenna couples with the interrogating electromagnetic radiation, charges the capacitor and powers the integrated circuit, which accesses the burned-in digital code.

This digital code is transmitted to the remote detector using the same antenna. The passive, radiofrequency marker may be either actively powered (i.e., via a battery) or passively powered (i.e., battery-free) which would therefore have an infinite life with extreme reliability. The RFID tag is encapsulated in a glass envelope so that it may be incorporated in a sponge or surgical pad without being affected by blood, moisture and the like. With this housing, the unit may also be laundered and sterilized without degrading its electronic circuit.

Generally stated, the invention involves the use of one or more RFID (radiofrequency identification) markers or transponders, secured to a variety of surgical implements, such as surgical sponges, gauze pads, instruments, and other items. A serious and recurrent problem occurring during surgical procedures is losing track of certain implements, leading to their being inadvertently left behind when the operation is complete and closed into the wound. This mishap, particularly when the overlooked item is a surgical sponge, oftentimes results in severe complications, even death.

The present invention overcomes this problem through the use of passive, glass encapsulated, RFID tags or markers that are secured to surgical implements. When equipped with such an RFID marker, the implement is readily located and identified by a stationary scanner that is mounted upon a roll-away cart or by a hand-held scanning antenna. A receiving unit detects a radiofrequency signal emitted by the marker representing the digital code burned-in the read-only memory or in the user programmable memory therein, permitting immediate identification and detection of any and all RFID-tagged implements remaining within the surgical cavity before the wound is closed.

Each implement is scanned by the RFID remote detector—once prior to introduction into the operative field, and again after completion of surgery, to create a recorded inventory. The wound is scanned at the conclusion of surgery, and if any tagged items are found to be still present, the surgeon is alerted and they are promptly removed before closing the wound, and subsequently individually identified. If an upper frequency tag is employed, scanning of the patient may also be carried out during surgery to determine which of the implements are contained within the surgical cavity and their disposition. Consequently, with the present invention, the retention of RFID-tagged implements is virtually eliminated. Since the digital code representing a sponge or surgical pad cannot be generated by anything other than the particular radiofrequency identification device implanted, detection is highly specific and there are generally no false signals.

A number of manufacturers produce these RFID tags or markers. Most notable of these manufacturers are Texas Instruments, Hughes Identification Devices, Destron-Fearing Corporation. Modern RFID tags also provide significant amounts of user accessible memory, sometimes in the form of read-only memory or user programmable write-once memory. The amount of memory provided can vary, and influences the size and cost of the integrated circuit portion of an RFID tag. Typically, between 128 bits and 512 bits of total memory can be provided economically.

For example, an RFID tag available from Texas Instruments of Dallas, Tex., under the designation "Tag-it" provides 256 bits of user programmable memory in addition to 128 bits of memory reserved for items such as the unique tag serial number, version and manufacturing information, and the like. Similarly, an RFID tag available from Philips Semiconductors of Eindhoven, Netherlands, under the designation "I-Code", provides 384 bits of user memory along with an additional 128 bits reserved for the aforementioned types of information.

The RFID tags under consideration herein operate at frequencies of from about 125 kHz through 950 MHz, although it is contemplated that the RFID tags may operate at any frequency. The low frequency RFID tags (typically operating at 125-134 kHz) can be tiny in size, relatively inexpensive to manufacture and are more resistant to loss of signal by tissue interference or from "shielding" by adjacent metal. When encased in glass or polymeric material, such RFID tags are capable of withstanding the effects of tissue fluid and various means of sterilization. However, because of their low bandwidth, such RFID tags cannot be read in bulk but rather must be identified one-at-a-time. At the upper frequencies (typically from 13.56 MHz through 950 MHz), the added bandwidth available permits systems that can reliably process multiple RFID tags in the interrogation zone during a short period of time.

In this surgical application, these upper frequency RFID tags with their added bandwidths then offer the added advantage of being capable of identification in bulk. This means that multiple tagged surgical implements can be identified regardless of whether the surgical implements are located on the instrument table or are within the patient wound. However, to their disadvantage, the upper frequency RFID tags are somewhat bulkier and more expensive to manufacture as compared to low frequency RFID tags. Furthermore, the signals of upper frequency RFID tags are more prone to absorption by body tissue and more susceptible to shielding by adjacent metallic objects. Because each type of RFID tags has advantages and disadvantages, the choice then of which type of RFID tag to utilize will most likely be individualized by the personnel of each institution.

On the other hand, if a low frequency RFID tag is employed, individual readings of each RFID tag must be taken when they are introduced into the operative field and again upon conclusion of surgery, and the two resulting inventories are compared to thereby account for all tagged items. When RFID tags must be individually handled in order to obtain a reading, lack of tag detection due to intervening tissue or shielding by metal will not occur. Consequently, despite their simplicity and bandwidth limitations, the low frequency RFID tags offer advantages owing to their resistance to attenuation, small size and reduced manufacturing cost.

Importantly, a modification is also hereby made to existing RFID technology which obviates the present need to provide anti-collision means in the detector system for RFID tags. At present, when conventional prior art RFID tag readers are presented with more than one identification code within the same interrogation zone, means must be provided to prevent the RFID tag from being "overwhelmed" by too much data. In the low frequency range, the RFID tag reader simply records the presence of two or more RFID tags as a negative reading: "no tag present." In the upper frequency range, anti-collision means may read the data from each RFID tag individually at alternating intervals.

Also described herein in is an improved detector system that may be employed at the conclusion of surgery. One version of the modified detector system includes an RFID tag reader, generally a hand-held unit that may have two possible responses: "no tag present", or "more than one tag present." The RFID tags may not necessarily be individually identified at this time and, therefore, anti-collision technology need not be included. If any RFID tags are found in the wound, they may be removed by the surgeon after which time they can then be specifically identified in one-at-a-time fashion.

An alternative version of the improved detector system is also described in greater detail below and combines the capability to detect both the presence and identity of RFID tags within a surgical wound. The identity of RFID tags may be detected in sequence with the act of determining the presence of such RFID tags. The detector system may also be configured to allow for either simultaneous and/or alternating detection and presence of RFID tags with the surgical wound. The detector system may be termed a "3-state" system due to its capability to indicate and display data relating to the existence of one of the following three states: "non-presence of RFID tags", "presence of at least one RFID tag", and displaying the "identification code of at least one of the RFID tags" within the scanned area (i.e., within the surgical wound), as will be described in greater detail below.

Also described below is a range-improving enhancement to the improved detector system wherein a tag assembly comprising 2 or 3 RFID tags may be secured to each surgical item with each of the RFID tags in each tag assembly being oriented orthogonally (i.e., at 90°) relative to one another in three-dimensional space. Attaching a tag assembly to a single surgical item results in a 20-100% increase in range for detecting the presence of RFID tags. Such an orthogonally-oriented arrangement of the RFID tags capitalizes on the ability of the improved detector system to detect the presence of multiple RFID tags.

DETAILED DESCRIPTION OF DRAWINGS

FIG. 1 is a schematic diagram showing an operation 10 in which an RFID identification and detection system is in use. Detection system 11, supported on a rollaway cart 17, is brought into close proximity to operating table 15, which supports a patient having an incision 16. Detection system 11 may be brought to the patient during surgery and prior to closure of incision 16. System 11 has interrogating antenna 12 providing detection functionality for RFID tag or markers incorporated within sponges or surgical pads. In an alternate embodiment, the detection system can be incorporated into a hand-held device 18, which is brought close to the patient by the doctor 19 for scanning the area of the surgical wound during and immediately upon conclusion of surgery but prior to wound closure.

In another alternate embodiment, the low frequency RFID marker tag described above is utilized. In this case, the detection system is brought next to the implement table and each tagged item is read with the hand-held scanner prior to and at the conclusion of surgery, before the wound is closed. The system 10 provides substantially error-free detection of RFID marker tags attached to various surgical implements present within the surgical wound. A digital broadcast signal received by the detector provides an audible and/or visible warning when a specific sponge or surgical pad is present within the surgical incision.

Figure 2:
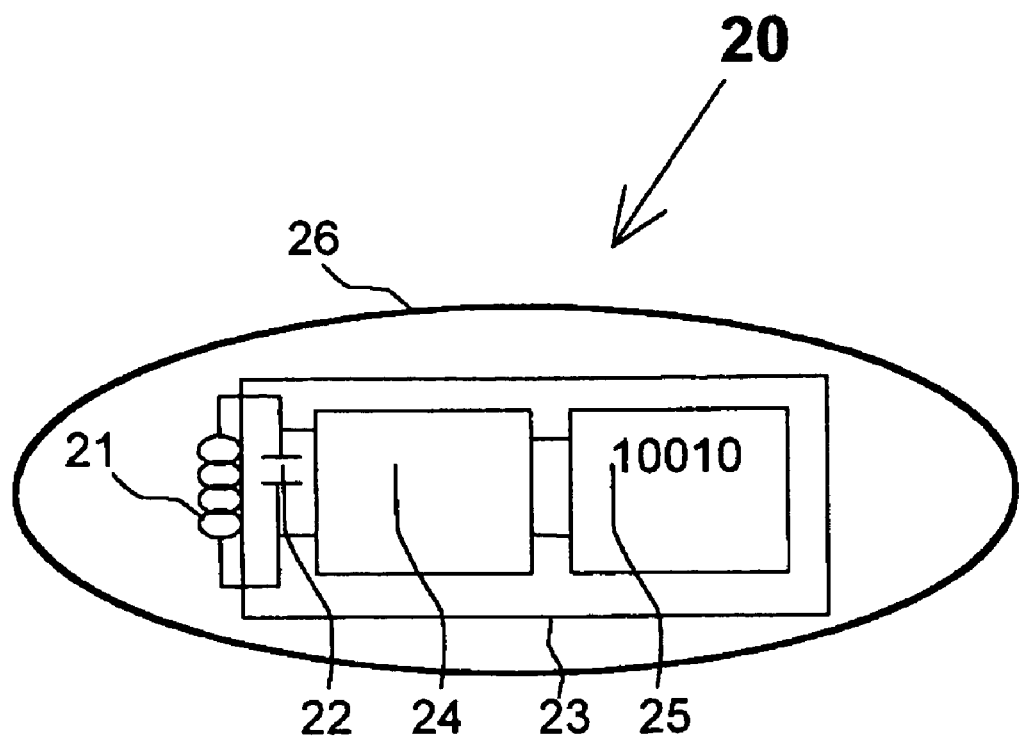
FIG. 2 is a diagrammatic representation of the details of construction of an encapsulated (RFID) marker.

Referring to FIG. 2 there are shown generally at 20 the details of the radiofrequency marker. The marker has an antenna 21, which receives a power pulse from a remote detector-interrogating antenna (not shown) to charge a capacitor 22. This capacitor 22 becomes the power source for the operation of the non battery-powered radiofrequency marker, which has an integrated switch having an integrated circuit 23 which has a reading function, carrier frequency modulating function 24 and a read-only or user programmable memory portion 25 with a burned-in code shown as '10010' in FIG. 2. The radiofrequency integrated chip together with the antenna 21 is encapsulated in enclosure 26, which is resistant to blood, saline solution or water.

Figure 3:
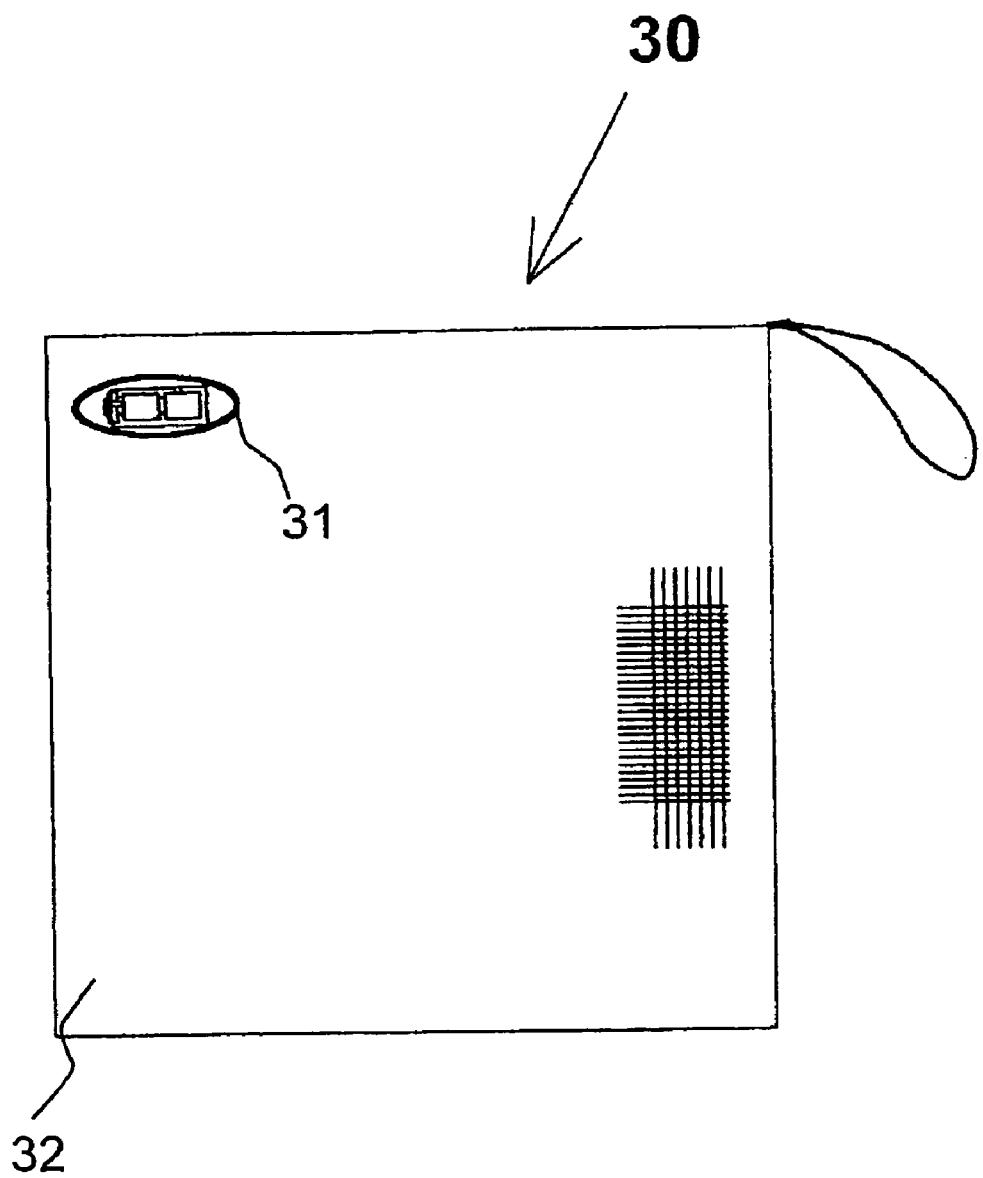
FIG. 3 shows at 30 the incorporation of an RFID marker in a surgical sponge (or laparotomy pad). The encapsulated radiofrequency marker 31 is affixed to sponge 32.

Referring to FIG. 3, there is shown generally at 30 certain details involving the incorporation of a RFID radiofrequency marker 31 in a surgical sponge 32. Marker 31 is incorporated inside sponge 32.

Figure 4:
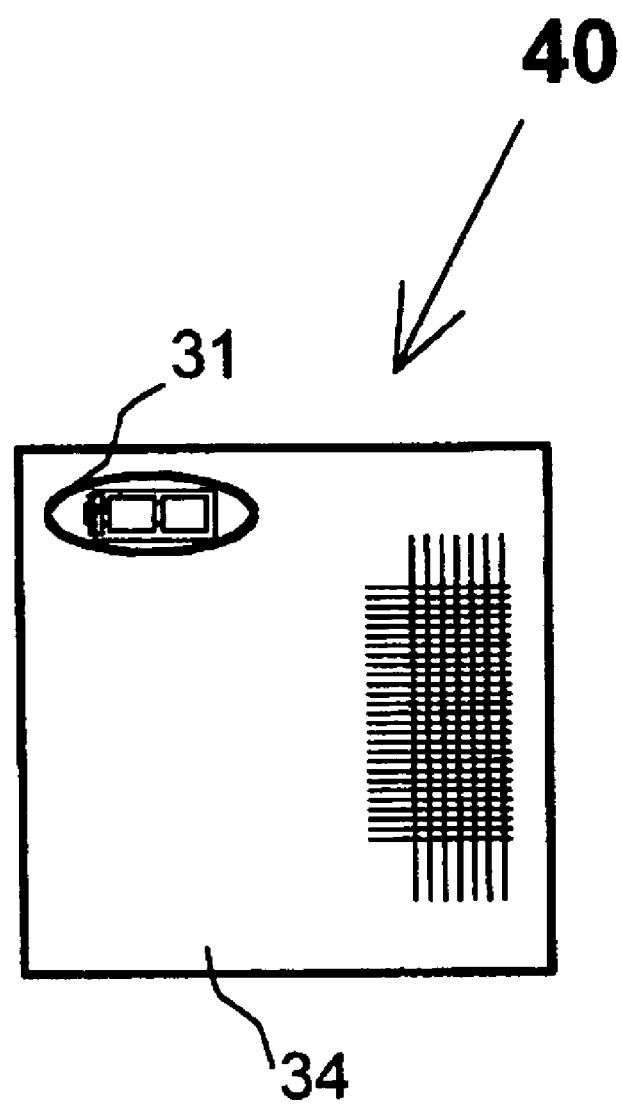
FIG. 4 shows at 40 the attachment of an RFID marker 31 to a 4" by 4" gauze pad 34. The encapsulated radiofrequency marker is shown sewn into gauze pad.

Referring to FIG. 4, there is shown generally at 40 certain details involving incorporation of a RFID radiofrequency marker 31 in gauze pad 34. The RFID radiofrequency marker 31 is sewn into gauze pad, as shown.

Figure 5:
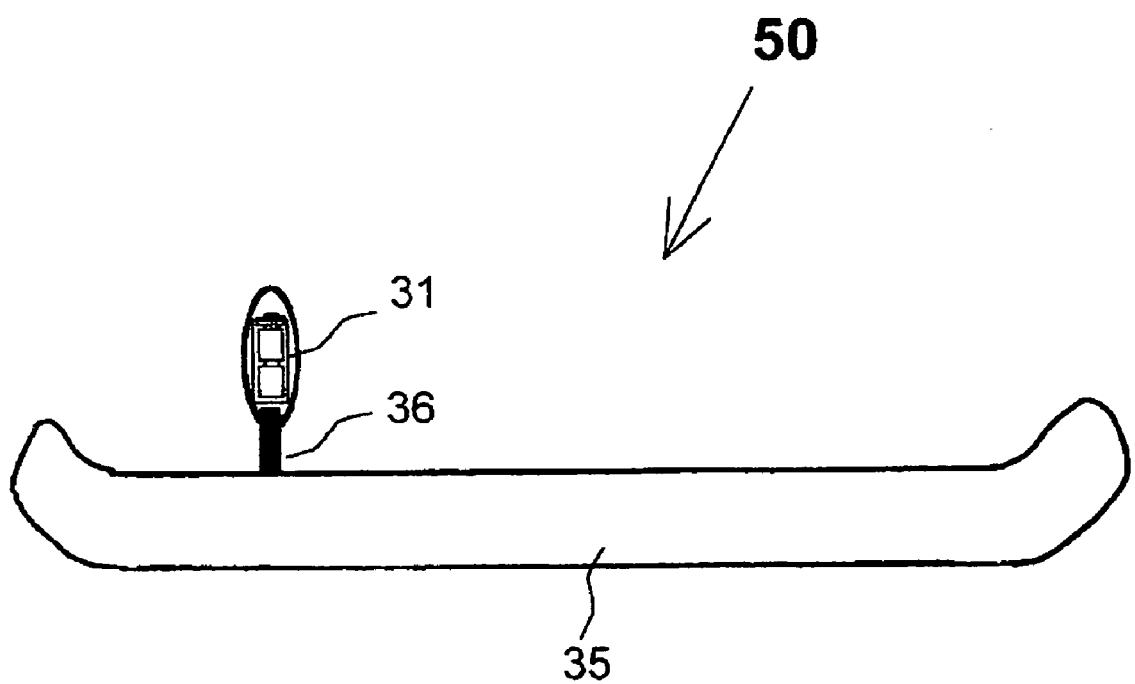
FIG. 5 shows at 50 the incorporation of an RFID marker in metallic instrument 35, a surgical retractor. The metallic surgical instrument 35 has a non-metallic extender 36 which carries encapsulated radio frequency marker 31 and separates the marker from the metallic surface of the surgical instrument preventing the possibility of shielding.

Referring to FIG. 5, there is shown generally at 50 certain details involving attachment of an RFID radiofrequency marker to metallic instrument 35, a surgical retractor. The metallic surgical instrument 35 has a non-metallic extender 36 which carries encapsulated radiofrequency marker 31 and separates the marker from the metallic surface of the surgical instrument preventing any shielding effect.

Figure 6:
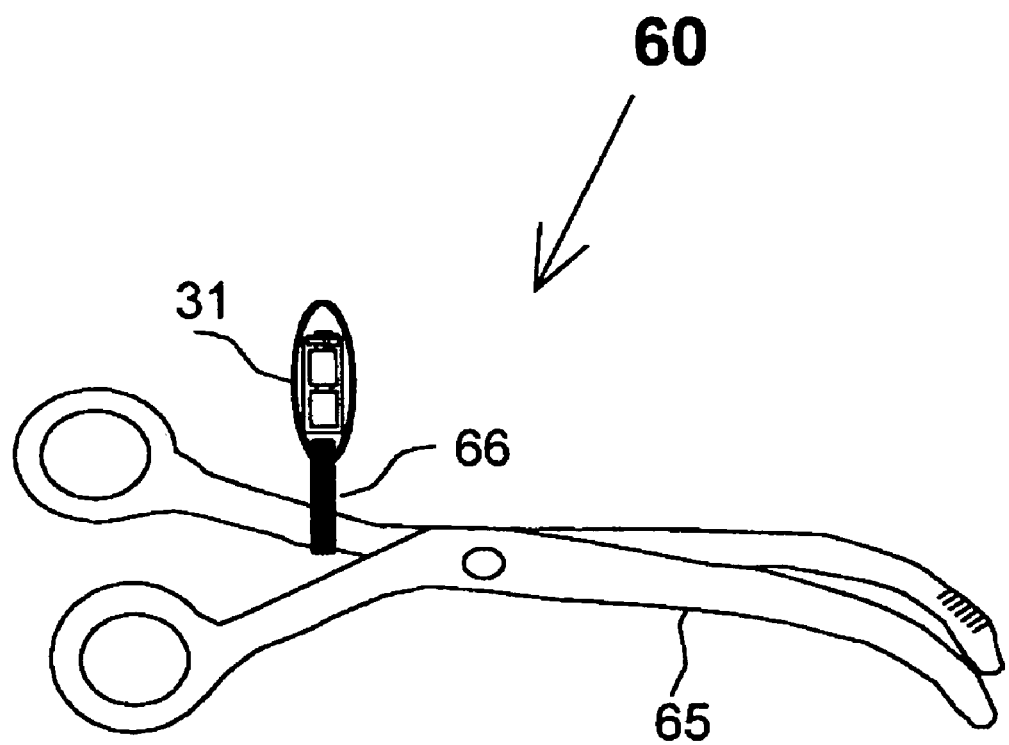
FIG. 6 shows at 60 the incorporation of an RFID marker in metallic instrument 65, a surgical clamp. The metallic surgical instrument 65 has a non-metallic extender 66 which carries encapsulated radiofrequency marker 31 and separates the marker from the metallic surface of the surgical instrument preventing the possibility of shielding.

Referring to FIG. 6, there is shown generally at 60 certain details involving attachment of an RFID radiofrequency marker 31 to metallic instrument 65, a surgical clamp. The metallic surgical instrument 65 has a non-metallic extender 66 which carries encapsulated radiofrequency marker 31 and separates the marker from the metallic surface of the surgical instrument preventing any shielding effect.

Figure 7:
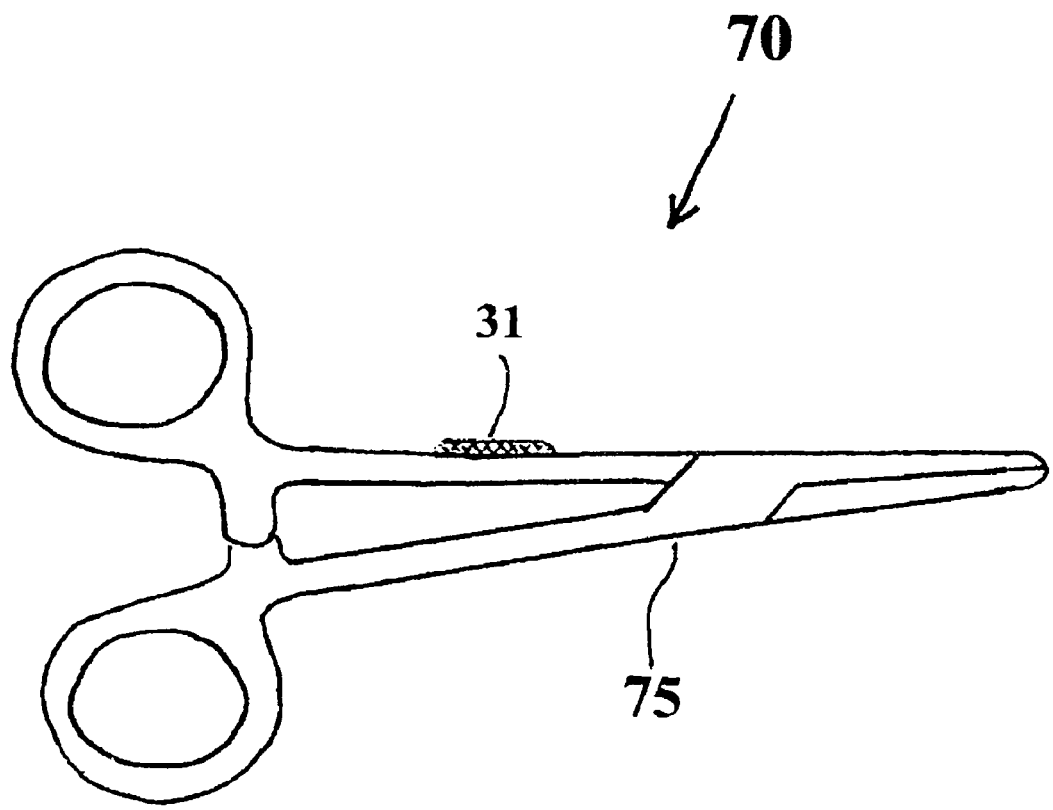
FIG. 7 shows at 70 the incorporation of a low frequency RFID marker 31 directly to the body of metallic instrument 75 surgical hemostat, without using the extender, which will not be needed in the case where individually readings are being performed.

Referring to FIG. 7, there is shown generally at 70 certain details involving attachment of a low frequency RFID radiofrequency marker 31 directly to the body of metallic instrument 75, a surgical hemostat, without use of a non-metallic extender. Direct attachment can be used when tags are to individually read and shielding is of no concern.

Significant advantages are realized by practice of the present invention. The key components of the surgical implement detector utilizing RFID tag or marker includes, in combination, the features set forth as follows. The surgical implement detector may include an integrated circuit, an antenna having wound copper wire on a ferrite core and a capacitor circuit. The integrated circuit may carry a read-only digital code or a user programmable code.

The integrated circuit may be capable of synthesizing and broadcasting the digital code signal using the ferrite antenna when powered by the charged capacitor circuit. The radiofrequency marker may be encapsulated in a hermetically sealed glass envelope to withstand laundering, sterilization procedures and forces applied during packaging. The encapsulated RFID tag or marker may also be secured to a surgical implement whether it is a surgical sponge, gauze pad, metallic surgical instrument, or other item used for surgery.

The surgical sponge or gauze pad or metallic surgical implement may be interrogated prior to surgical incision closure by a remote, fixed antenna or a hand-held detector antenna that broadcasts a frequency signal in the range of 30 KHz to 2.45 GHz, and preferably about 125 kHz or 13.56 MHz, or 850 to 950 MHz. The interrogation signal from the antenna may be attached to remote, fixed detection system or the hand-held antenna attached to the same system charging the capacitor circuit of the radiofrequency marker in order to provide power for operation of the integrated circuit.

The operation may include reading the digital code, synthesizing a PWM, PPM or FSK modulated broadcast carrier signal representing the digital code, and broadcasting the digital code signal through the antenna to the antenna coil of the detector. The detector may also be operative to interpret the received digital code in the broadcast modulated carrier signal and match it with code created by previously scanned digital code data from sponges, surgical pads or metallic surgical implements appointed for use during the surgical procedure. The surgical implement detector may be used for detecting sponges, surgical pads or metallic surgical implements retained within the surgical cavity.

Such detection may be performed by using the remote, fixed antenna reader or preferably the hand-held reader in order to identify each implement once upon introduction into the operative field and before insertion into the wound and again upon conclusion of surgery and recording such readings separately. The handheld detector may be used in the newly introduced mode whereby the wound is scanned at the conclusion of surgery solely for determination of whether any tags are present or not, without making any identification. Both readings may be compared to insure that they match meaning that all RFID-tagged items have been accounted for and using such record to prepare an inventory for charging purposes.

Referring now to FIGS. 8a-20, also provided herein is an improved RFID identification and detector system 100, which, as was mentioned above, allows for the detection of multiple RFID tags 112 without the problems of data collision. The detector system 100 is also configured to allow for the detection of a single RFID tag 112 using the unique arrangements of a remote detector unit 106 in its power integrator 140 and constellation discriminator 146 versions which will be described in detail below. The detector system 100 of the present invention applies to semi-conductor based RFID tag 112 systems of both passive and active varieties and may be configured to operate across all frequency bands including the intermediate frequencies. The improved detector system 100 may further include the ability to detect presence and identity, either simultaneously, sequentially, or alternately, within a surgical wound. The detector system 100 may be termed a "3-state" system due to its ability to indicate and/or display data relating to the presence or non-presence of RFID tags 112 and/or identification code of the RFID tags 112 within the scanned area.

Figure 8A:
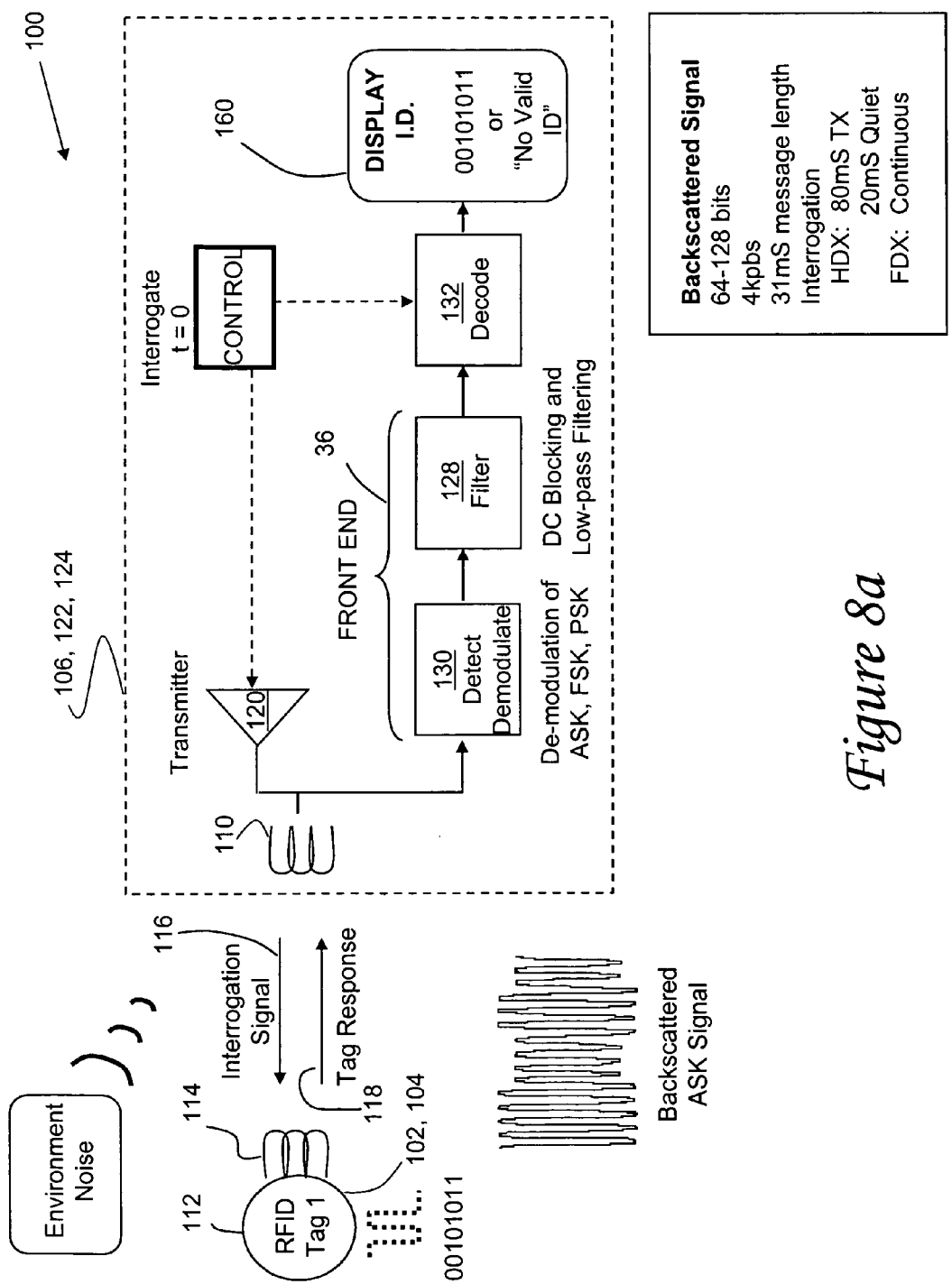
FIG. 8a is a schematic diagram of a detector system and illustrating the activation of a single RFID tag by a remote detector unit wherein the RFID tag returns a modulated carrier frequency (i.e., a tag response) in response to a carrier frequency (i.e., interrogation signal) transmitted by the remote detector unit.
Figure 86:
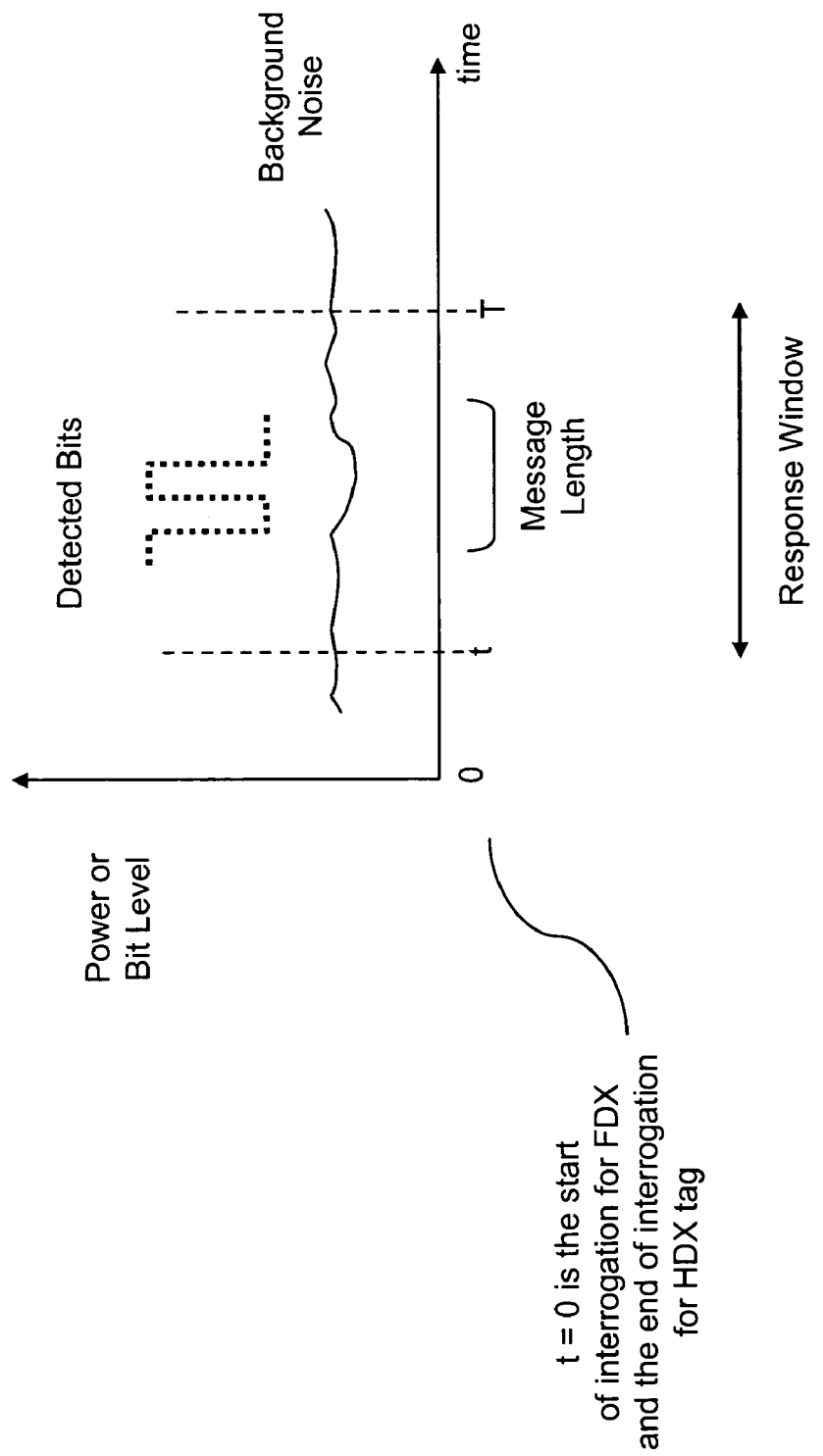

Referring first to FIG. 8a, shown is a detector system 100 which is shown with a single RFID tag 112. As is well known, detector systems 100 similar to that shown in FIG. 8a employ a remote detector unit (e.g., a handheld unit) which may have an interrogating antenna 110 configured to transmit an interrogation signal 116 (i.e., a carrier frequency). Typically, such remote detector units 106 of the prior art are capable of transmitting the interrogation signal 116 over a small area or range (i.e., distance). The RFID tag 112, which may be attached to the surgical item 102, may include an RF antenna 114 which is coupleable to the interrogating antenna 110 when the RFID tag 112 and remote detector unit 106 are within range of one another, hereinafter referred to as "message range."

The RF antenna 114 receives the carrier frequency from the interrogating antenna 110 and passes it on to an integrated circuit 122 which may further include a memory device 124 capable of impressing an identification code onto a modulated carrier frequency. The modulated carrier frequency is then transmitted as a tag response signal 118 which, in low frequency RFID tags 112 that are passively powered, occurs by backscatter in full duplex mode (FDX). In this regard, backscatter occurs by altering loading of the RF antenna 114 which changes a magnetic field of the interrogating antenna 110 (i.e., of the remote detector unit 106). This change in the magnetic filed creates a tiny fluctuation in the amplitude-modulated (ASK-amplitude shift keyed) signal in the example shown. In half duplex operation (HDX), energy from the RFID tag 112 is stored up during the transmission of the interrogation signal 116. The RFID tag 112 may include an onboard transmitter 120 which produces a modulated signal similar to that of the FDX RFID tags 112, usually with ASK modulation.

It should be noted that the RFID tags 112 may be configured to be passively powered or actively powered or a combination thereof. Passively powered versions may receive power from the interrogation signal 116 transmitted by the remote detector unit 106. In this regard, top level modulation may of any variety including ASK (amplitude), Phase Shift Keying (PSK) and Frequency Shift Keying (FSK) modulation which may also be frequently used with the ASK signal. For passively powered versions, the RFID tags 112 may each include a capacitor 148 connected to the RF antenna 114 and which is then chargeable by the carrier frequency (i.e., the interrogation signal 116 from the remote detector unit 106) in order to provide power to the integrated circuit 122 contained within the RFID tag 112.

Alternately or in combination therewith, the RFID tag 112 may be also actively powered and may include a battery for powering the integrated circuit 122. Despite their ability to transmit over a longer range, actively powered RFID tags 112 suffer from the deficiency that the battery itself has a finite life and must either be replaced or the RFID tag 112 must be replaced on the surgical item 102. On the other hand, passively powered RFID tags 112 have an essentially infinite life and may be of a simpler construction than actively powered RFID tags 112. Furthermore, potential risks associated with battery leakage in an actively powered RFID tag 112 is another consideration.

Referring still to FIG. 8a, the RFID tag 112 can be seen transmitting a tag response signal 118 (i.e., modulated carrier frequency) which is then detected by the remote detector unit 106 at the interrogating antenna 110 and which is then passed on to a front end circuit 126. The front end circuit 126 may include an envelope detector 176 which may be configured as a simple diode 174 in order to collect and de-modulate the modulated carrier frequency (i.e., the tag response signal 118). However, other components may be utilized for detecting the tag response signal 118 emitted by the RFID tags 112 including a heterodyne receiver, a phase-locked loop (PLL), or a carrier direct sampling circuit 152. The carrier direct sampling circuit 152 may directly sample received modulated carrier frequencies from the RFID tag 112 such as by utilizing a micro-processor. The tag response signal 118 sent by the RFID tags 112 are typically 64-128 bits long and contain CRC bits in order to check for data transmission errors. The tag response signal 118 may further include a header, the object type, the company identity and the actual serial number of the RFID tagged 112 item 102.

Referring still to FIG. 8a, the prior art detector system 100 strips the carrier from the tag response signal 118 leaving the modulation. The front end circuit 126 may further include a filter 128 which is configured to remove direct current (DC) and high frequency interference in the carrier components in order to leave a raw bit stream. A decoder 132 may further be included in the front end circuit 126 to square up the data and begin to assess bit states via zero-crossings or other means.

If the decoder 132 verifies that a valid message has been received from the RFID tag 112, the message is displayed such as via a display device 160. If bit errors are found in the tag response signal 118 or the message is deemed invalid, a message such as "no valid ID" or similar message may be displayed. The detected bits in the tag response signal 118 must be at a level that is significantly (e.g. 10-15 dB) above an environmental noise level such as is illustrated in the upper left hand corner of FIG. 8a. Signals included in the environmental noise may in this manner interfere with reliable detection of RFID tag 112 response signals. Therefore, detected bits must be significantly above the environmental noise floor level in order to increase the likelihood that a valid message is received at the remote detector unit 106.

As was noted above, prior art detector systems 100 such as that illustrated in FIG. 8a may have a range that is limited to four inches or less for a typical 125-134 kHz application using HDX or FDX RFID tags 112. However, in human surgery, patients may have a dozen or more metallic or non-metallic instruments residing within the body cavity during the operation. A range of eight inches or more is typically required in order to adequately scan the full depth of an average patient's body in order to detect the presence of RFID tagged 112 items 102. Unfortunately, such a range is more than double the range at which detection of RFID tags 112 in a patient may be reliably performed. This is because in magnetic coupling, power contained within the tag response signal 118, and which is received by the remote detector, decreases in proportion to the cube of the distance to the RFID tag 112. For free-space coupling, power contained within the tag response signal 118 and which is received at the remote detector unit 106 decreases in proportion to the square of the distance to the RFID tag 112. In summary, as the distance between the remote detector unit 106 and the RFID tag 112 increases, signals transmitted by the RFID tag 112 become weaker which results in the creation of bit errors which, ultimately, reduces the reliability of the readings.

Referring briefly to FIG. 8b, shown is a graph of power or bit level contained within the RFID tag response signal 118 as a function of time. A plot of detected bits is shown above a plot of environment (i.e., background) noise. For Full Duplex (FDX) operation, zero on the plot represents the start of interrogation signal 116 transmission by the remote detector unit 106. For Half Duplex (HDX) operation, zero represents the end of transmission of the interrogation signal 116 by the remote detector unit 106. The tag response signal 118 is received within a response window represented as the distance between "t" and "T" as shown in the graph in FIG. 8b. Detection of the RFID tag 112 may therefore occur during the response window when the power or bit level contained with the tag response signal 118 is above the level of the environmental noise.

Figure 9A:
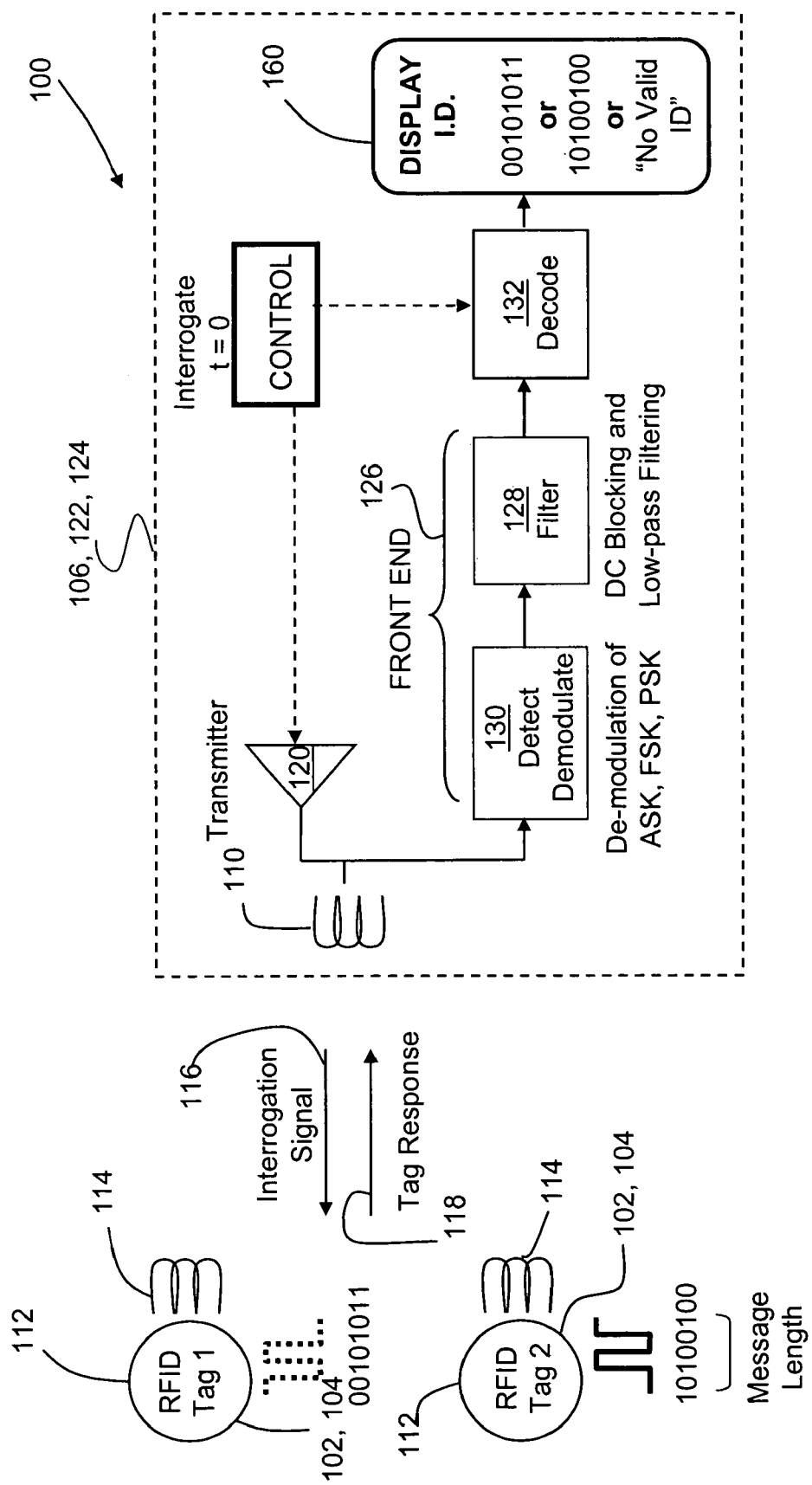
FIG. 9a is a schematic diagram of a prior art remote detector unit wherein two RFID tags are activated by the interrogation signal during the predetermined response time resulting in a "data-collision" between bits contained in the RFID signal over at least part of the message resulting in a "false negative" indication (i.e., an indication of non-presence of an RFID tag when in fact two RFID tags are present)
Figure 9B:
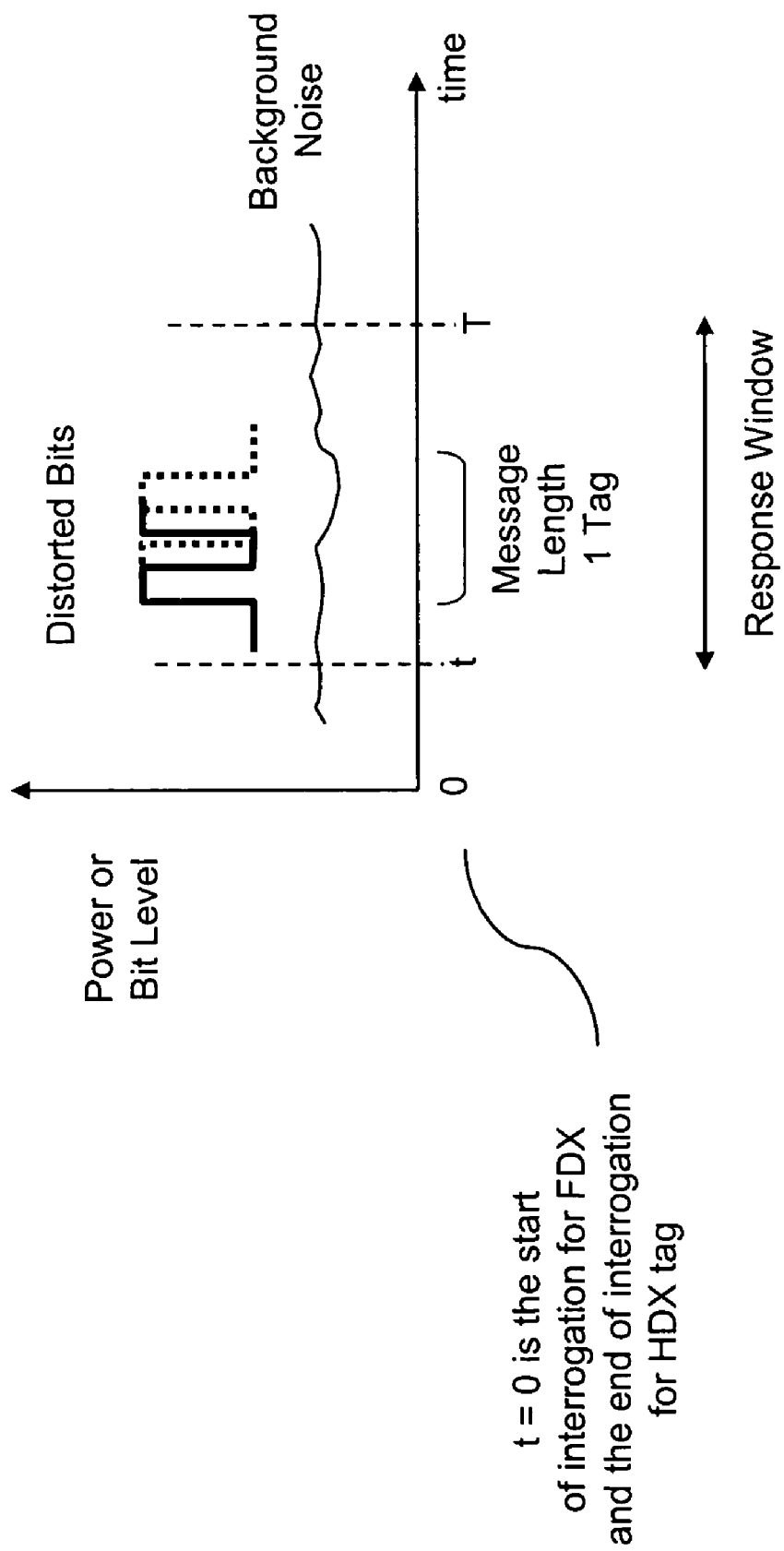
FIG. 9b is a graph of signal power versus time illustrating an overlap occurring between tag bits contained within the respect of RFID tag signals and resulting in the "false negative" reading due to scrambling of the 1's and 0's in the tag bits of the RFID tag signals.

Referring now to FIGS. 9a and 9b, shown is the detector system 100 with multiple (i.e., two or more) RFID tags 112 within range of the remote detector unit 106. As was earlier mentioned, collision between tag bits contained within the tag response signals 118 typically occurs over at least part of the message which then scrambles the received 1's and 0's such that the remote detector unit 106 is incapable of indicating when a valid RFID tag 112 has been detected. In the case of an envelope detector 176 in the remote detector unit 106, if signals from either the first RFID tag 112 or the second RFID tag 112 are a "1", the received result is a "1". The remote detector unit 106 may then display either the identification code for the first RFID tag 112, the second RFID tag 112, or indicate "no valid ID".

In summary, the above discussion in reference to FIGS. 8-9 demonstrates why conventional detector systems 100 are incapable of distinguishing between results arising from an RFID tag 112 being out of range of the remote detector unit 106 and between two RFID tags 112 whose tag response signals 118 collide with one another. In other words, conventional detector systems 100 are not capable of distinguishing between "no RFID tag 112" and "no valid RFID tag 112". A "no valid RFID tag 112" response could mean that there are two or more RFID tags 112 present within the patient wound, or, that there are no RFID tags 112 present. Therefore, the inventor submits that there is no reliable way, using conventional detector system RFID technology, to verify that no surgical instruments or implements have been left in a patient wound absent the incorporation of more expensive collision control tag technology into the detector system 100.

Figure 10:
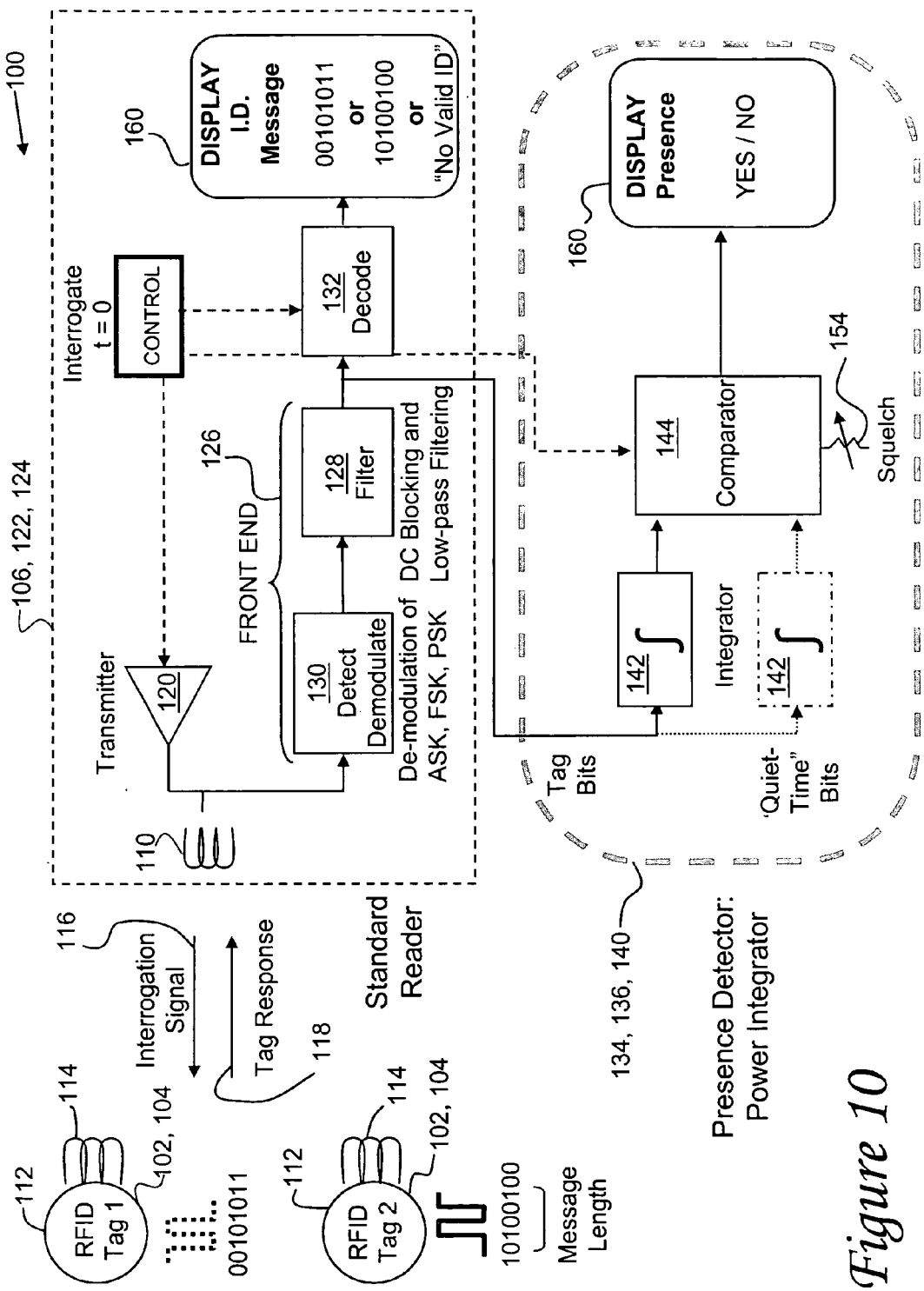
FIG. 10 is a schematic diagram of a detector system in an embodiment of the present invention including a presence detector that is specifically configured to avoid "data-collision" between signals transmitted by competing RFID tags and wherein the power contained within the RFID tag is integrated over time by a power integrator for comparison to an environmental noise level measurement taken during a quiet period.
Figure 11:
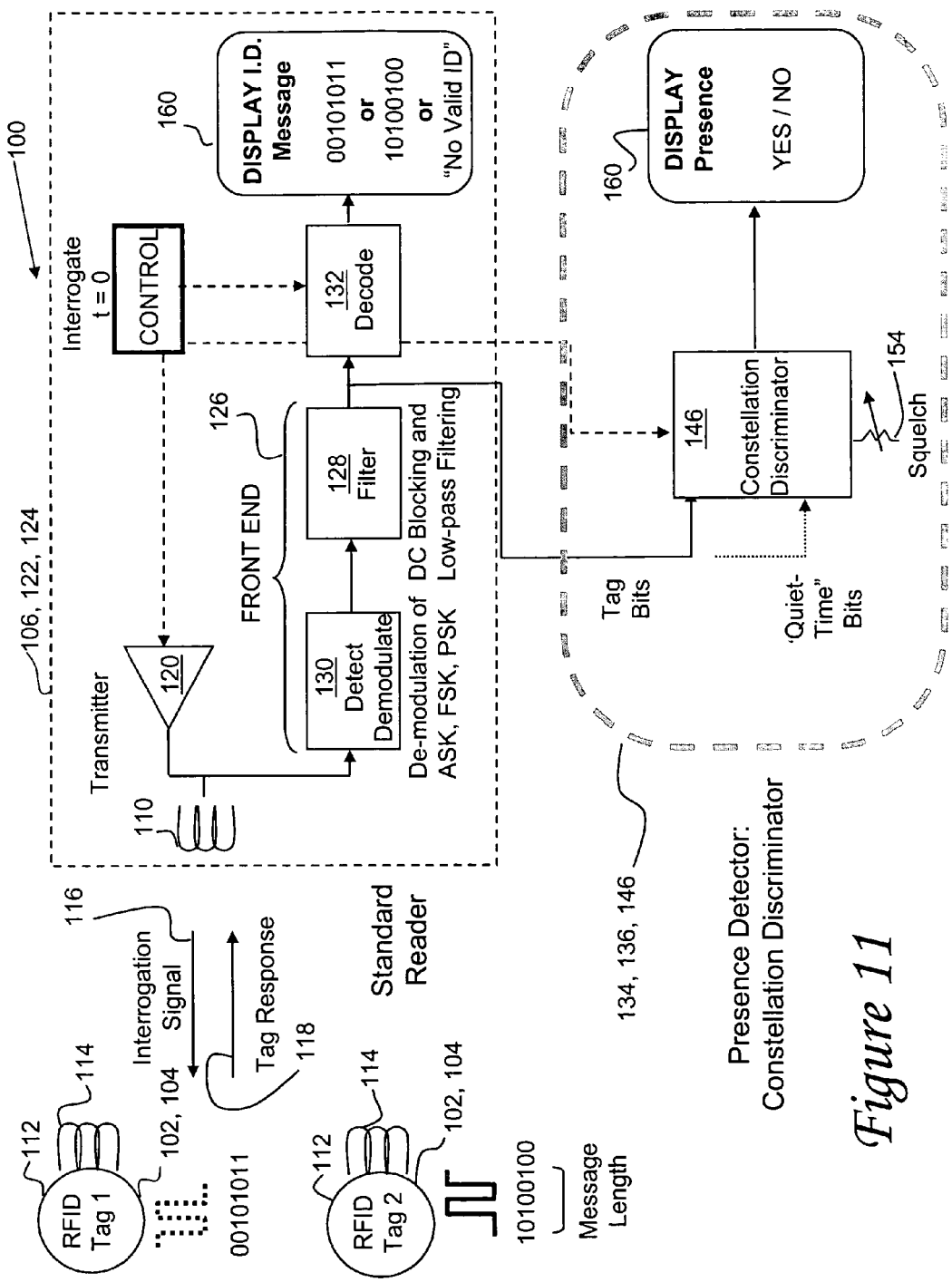
FIG. 11 is a schematic diagram of the detector system in a further embodiment having a constellation discriminator configured to compare bits contained within RFID tag signals during the predetermined response time period for comparison to a pattern of bits within a predetermined reference constellation of the environment sample during the quiet period.

In light of the above noted deficiencies associated with prior art detector systems 100, reference is now made to FIGS. 10 and 11 for an improved detector system 100 which provides the capability to detect the presence of one or more RFID tags 112 without necessarily identifying the RFID tags 112 during a given sweep of the patient wound. As was earlier mentioned, the detector system 100 may also be used to detect a single RFID tag 112 within range of the remote detector unit 106 using either the power integrator 140 and/or the constellation discriminator 146 circuits as will be described in detail below. In its broadest sense, the detector system 100 comprises a presence detector 108 for detecting a plurality of RFID tags 112 within a "presence range" therebetween. Importantly, the detector system 100 includes a signal reader 136 incorporated into the front end circuit 126 and which is specifically configured to receive the modulated carrier frequencies from the RFID tags 112 during a predetermined response time period and then compare the modulated carrier frequencies to a reference level for determining the presence of RFID tags 112 within the presence range. The signal reader 136 is the receiver portion of the remote detector unit 106.

As can be seen in FIG. 10, the improved detector system 100 includes circuitry similar to that shown and described above for FIGS. 8a and 9a for the prior art detector system 100. However, the detector system 100 is modified to include the signal reader 136 which may be configured as either a power integrator 140 and/or as a constellation discriminator 146 which will be described in further detail below. In this regard, the presence detector 108 includes the interrogating antenna 110 which transmits the carrier frequency to the plurality of RFID tags 112 which are attached to respective items 102 such as surgical implements 104. Each RFID tag 112 includes an RF antenna 114 which is coupleable to the interrogating antenna 110 of the presence detector 108. The presence detector 108 may be coupled to the RFID tags 112 when the antennae thereof are within the presence range. The innovative circuit of the RFID tag 112 may include a memory device 124 which impresses an identification code onto the modulated carrier frequency which is contained in the signal and which is transmitted back to the presence detector 108 by the RFID tag 112.

The interrogating antenna 110 receives signals from at least one of the following: (1) signals transmitted by at least one of the RFID tags 112, (2) signals transmitted by a combination of environmental noise and at least one of the RFID tags 112. The presence detector 108 further includes the front end circuit 126 as was described earlier and which comprises a signal detector 134 for detecting the modulated carrier frequencies in the signal. The signal reader 136 is connected to the front end circuit 126 and can be configured as the power integrator 140 or as the constellation discriminator 146. The signal reader 136 determines the presence of RFID tags 112 within the presence range and is operative to cause an indicator device 162 that is connected to the signal reader 136 to display (i.e., via a digital reader, an audible signal, a flashing light, etc.) the presence of RFID tags 112 within the presence range.

If configured as the power integrator 140, the signal reader 136 comprises an integrator unit 142 that receives modulated carrier frequencies during the predetermined response time period and sums power contained in such signals by integration thereof. The power integrator 140 further includes a comparator 144 connected to the integrator unit 142 and which is configured to compare integrated signal power to the reference level (i.e., the environmental noise level). The signals that are received by the integrator unit 142 may be either a detected voltage corresponding to the carrier frequency, or, demodulated bits corresponding to a composite of RFID tag 112 transmission bits. The indicator is configured to indicate the presence of RFID tags 112 when the integrated signal power is greater than the reference level.

The predetermined response time period may typically be 20 mS for typical HDX operation. The summing of the power may be facilitated by using either a simple capacitor 148, an operational amplifier 150 whose function is to integrate, or a sampling circuit 152 that may be controlled by a microprocessor 172. The front end circuit 126 may include a demodulator 130 which is configured to remove the carrier from the signals received by the RFID tags 112 and thereby recover modulating messages contained there within. The comparator 144 may be constructed using an operational amplifier 150 and which is configured to compare the integrated power bits within the RFID tag response signals 118 to the reference level which is established during a quiet period.

As was mentioned above, the quiet period may be a time during which measurement is taken of the environmental noise level and which may be performed during HDX operation, or, alternatively, may be a measurement taken either in FDX or HDX operation with the interrogating antenna 110 and RF antenna 114 being either non-transmitting or outside of the presence range (i.e., non-coupled to one another). The comparator 144 is the decision-making component of the power integrator 140 and includes "Yes/No" circuitry with a threshold.

In this manner, the power integrator 140 may detect the presence of RFID tags 112 when integrated power exceeds the reference level providing a "Yes" response which indicates that one or more RFID tags 112 may be present. As can also be seen in FIG. 10, the quiet period reference measurement may be augmented by the use of an adjustable squelch which is shown connected to the comparator 144. The adjustable squelch circuit 154 is specifically configured to allow for selection of the squelch setting which is the point above the environmental noise level by which comparison thereof to the integrated signal power occurs. In this regard, the adjustable squelch circuit 154 allows for a desirable trade-off between a "false positive" and an increase in the presence range.

For example, a lower squelch setting, one that is closer to the environmental noise level, may allow for more frequent readings of "false positives" (i.e., less frequent readings of "false negatives") but which also allows for an increase in the presence range. Here, the presence range can be thought of the distance at which a reliable NO is obtained (e.g. 90% of the time). The squelch setting may be determined by a calibration procedure wherein the squelch is adjusted to a signal offset level corresponding to the desired reliability of presence detection. The squelch setting may be calibrated by a number of methods. For example, the squelch setting may be preset or it may be user adjustable during operation of the detector system 100. The calibration procedure may comprise an adjustment to the amount of offset according to a predetermined table that may be generated by a series of reliability tests correlating reliability to offset setting (e.g., 0 dB generates 50 percent reliability; 6 dB generates 90 percent reliability of the detector system 100, etc.).

Figures 14A, 14B:
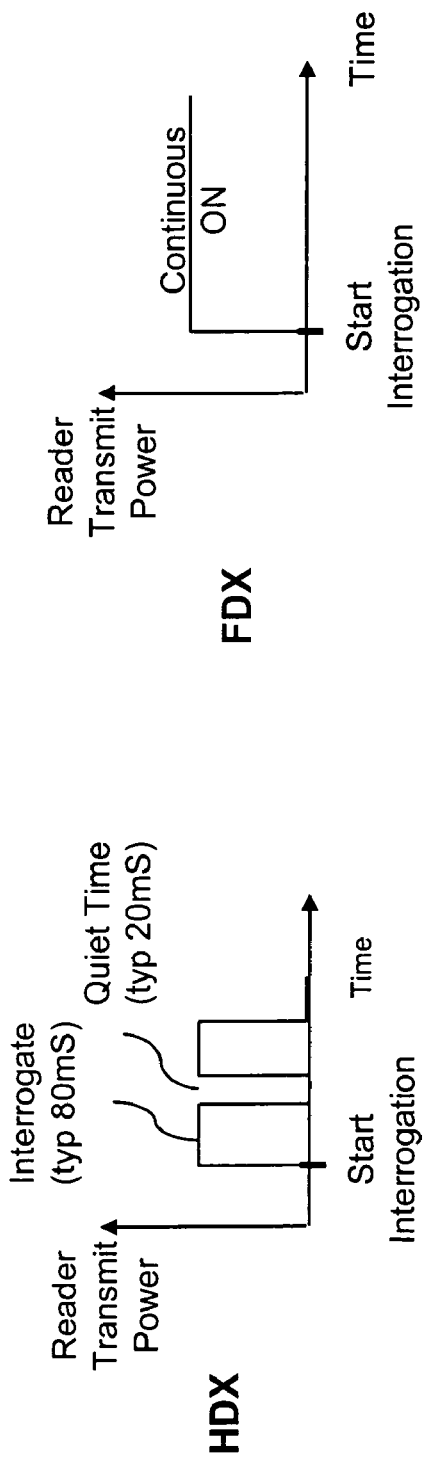
FIG. 14a is a graph of interrogation signal power versus time during half duplex operation of the detector system and illustrating a sequence of calibration wherein the detector system is operative to detect RFID tags over an interrogation time period followed by a quiet period operation wherein the remote detector unit and RFID tags are either non-transmitting or are out of the range of one another.
FIG. 14b is a graph of interrogation signal power versus time during full duplex operation wherein the detector system may be calibrated by keeping the remote detector unit and the RFID tag(s) out of the range of one another.

Regarding calibration, in an HDX system, calibration of quiet time noise can be made during the intervals between transmissions (i.e., of interrogation signals 116) by the presence detector 108. In an FDX system, once initiated, transmission of the interrogation signals 116 by the presence detector 108 is preferably continuous as is shown in FIG. 14b. Therefore, for FDX operation, the presence detector 108, which is a remote device apart from the RFID tags 112, must be moved away from any of the RFID tags 112 (i.e., out of the presence range) in order to obtain a quiet time reference level. In contrast, for HDX operation, calibration is represented by FIG. 14a wherein calibration occurs during intervals between transmissions of interrogation signals 116 by the presence detector 108.

The quiet period is preferably of substantially the same length as the predetermined response time period during presence detection. Alternatively, the length of the quiet period may be longer than that of the predetermined response time period. In addition, it is contemplated that the presence detector 108 may be configured to perform additional quiet period sampling during use of the detector system 100 in order to improve reliability without sacrificing range. For example, when the presence detector 108 is not being used, it may be configured to average the reference level (i.e., the environmental noise level measurements) over time. Furthermore, the presence detector 108 may be configured to detect and discount extraneous environmental noise such as a pulse from a fan operating in the same room. The presence detector 108 may be further configured to provide a reliability warning such as via the display device 160 in order to alert operating personnel of the potential invalidity of readings.

Referring now to FIG. 11, shown is an embodiment of the detector system 100 wherein the signal reader 136 is configured as the constellation discriminator 146. The constellation discriminator 146 essentially comprises a demodulator 130 and a comparator 144. The demodulator 130 is connected to the front end circuit 126 and is specifically configured to remove the carrier from the signals and recover a modulating message contained there within. The comparator 144 is connected to the demodulator 130 as can be seen in FIG. 11 and is operative to receive bits contained within the modulating message during the predetermined response time period and to compare a pattern of the bits to a predetermined reference constellation.

The bits received by the constellation discriminator 146 are comprised of either uncorrupted bits transmitted by at least one of the RFID tags 112, or, corrupted bits transmitted by a combination of environmental noise and at least one of the RFID tags 112. Upon determining that the bit pattern is distinguished from the reference constellation, an indicator device 162 is configured to indicate (i.e., via a digital readout, an audible signal or a flashing light signal, etc.) the presence of RFID tags 112 within the sweep area (i.e., patient wound area). The specific configuration of the constellation discriminator 146 may depend in part upon the modulation type used (e.g., "FSK"), the encoding (e.g., bi-phase), and the number of RFID tags 112 expected to be found within the sweep period.

The constellation discriminator 146 may be configured simply as a bit counter 156 that is configured to record the ratio of 1's to 0's that are contained within the bit pattern. Nominally, the bit pattern contained within the signals from the RFID tags 112 will contain 50 percent 1's (i.e., an equal proportion of 1's and 0's). The bit counter 156 can exploit this characteristic to determine the bit pattern type by comparing the nominal ratio to the ratio of the bit pattern received from the comparator 144.

The reference constellation is a measurement of the environmental bit pattern which is preferably taken during the quiet period. As was previously mentioned, the quiet period may occur during HDX operation when the RFID antenna and the interrogating antenna 110 of the RFID tags 112 and presence detector 108 are either non-transmitting or are out of range from one another. The same may be true during FDX operation of the detector system 100.

Figure 13A:
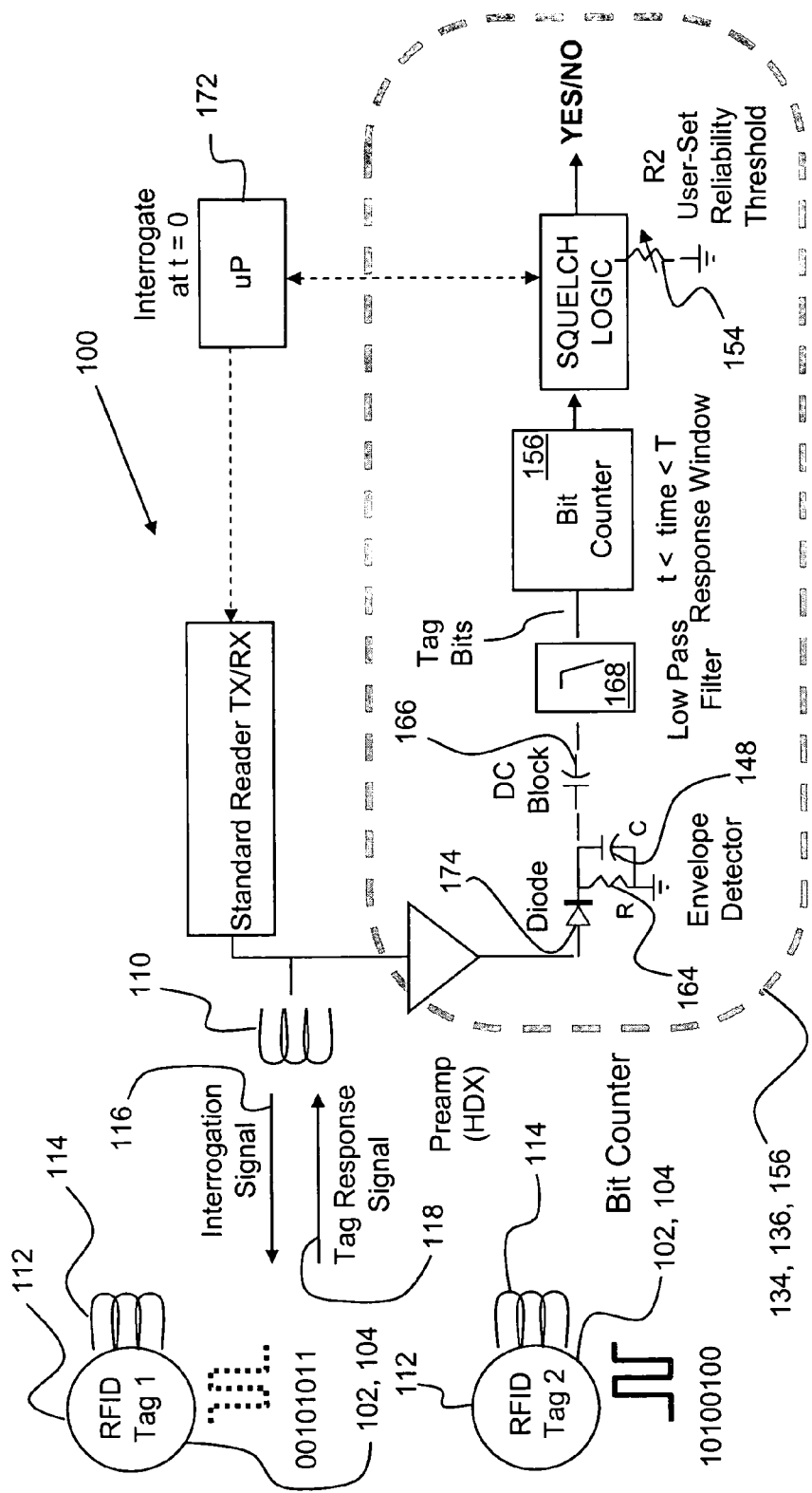
FIG. 13a is a schematic diagram of an embodiment of the constellation discriminator having a bit counter which is operative to sum signal bits from the RFID tags over the predetermined response time for comparison to an environmental reference constellation measurement taken during the same predetermined response time period.
Figures 13B, 13C:
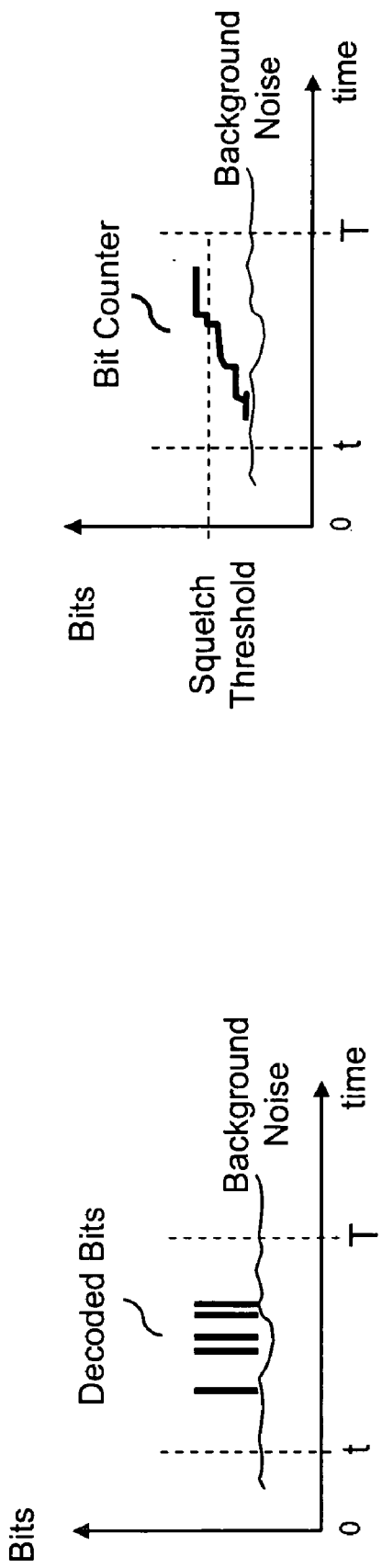
FIG. 13b is a graph of signal bits versus time and illustrating a plot of decoded bits and a plot of the environmental noise level measurement.
FIG. 13c is a graph of signal bits versus time and illustrating a bit counter plot as well as a plot of the squelch threshold which may be adjustable to allow selectability of the point at which the detector system indicates "false positive" readings and detection range.

As seen in FIGS. 13a-13c, shown is a specific embodiment of the constellation discriminator 146 incorporated with the detector system 100 of the present invention wherein the presence detector 108 transmits an interrogation signal 116 as a continuous wave signal (e.g., 134 kHz) through it's interrogating antenna 110 stimulating a nearby RFID tag(s) 112. The continuous wave signal may be 100 volts or more in peak-peak amplitude. An ASK-modulated signal containing, for example, 96 bits is then received by the interrogating antenna 110 and is then routed to the envelope detector 176. Composed of one or more diodes 174 and related circuitry, the forward current of this alternating (i.e., AC) signal conducts through the diode 174 to ground through capacitor 148 "C" as shown in FIG. 13a. Resistor 164 "R1" and capacitor 148 "C" form a low pass filter 168 which simultaneously attenuates the 134 kHz carrier while passing on the de-modulated base band signal (e.g., 4 kHz) of a substantially lower frequency.

As can be seen in FIG. 13a, a DC block 166 removes the accumulated carrier DC voltage and passes the base band signal (e.g., 1-4 kHz) onto the low pass filter 168. The low pass filter 168 more specifically seeks to remove environmental noise that is just above the highest modulation signal (e.g., 4 kHz) while passing the base band signal onto the bit counter 156. The bit counter 156 adds up the number of base band signal bits during the predetermined response time period (i.e., the response window as shown in FIGS. 13b and 13c) which may be about 20 mS in duration. The bit counter 156 creates the highest possible count (e.g., 60) which is then routed to the comparator 144 circuit in the squelch logic. The squelch logic contains a reference measurement made during the quiet period and establishes a threshold above which reliable detection of an RFID tag(s) 112 may occur (e.g., 50).

As was previously mentioned, the squelch may be an adjustable squelch circuit 154 that is configured to allow for selection of a squelch setting. In this regard, a switch, thumbwheel or pre-programming (e.g., as indicated by variable resistor 164 R2 as shown in FIG. 13a) may be available to allow the user to augment the squelch setting in order to fine tune the detector system 100 as a compromise between "false positives" and presence range (i.e., the range between the presence detector 108 and the RFID tag 112). If the bit count exceeds the reference setting, the detector system 100 is configured to indicate and/or display the presence of an RFID tag 112.

Figure 12A:
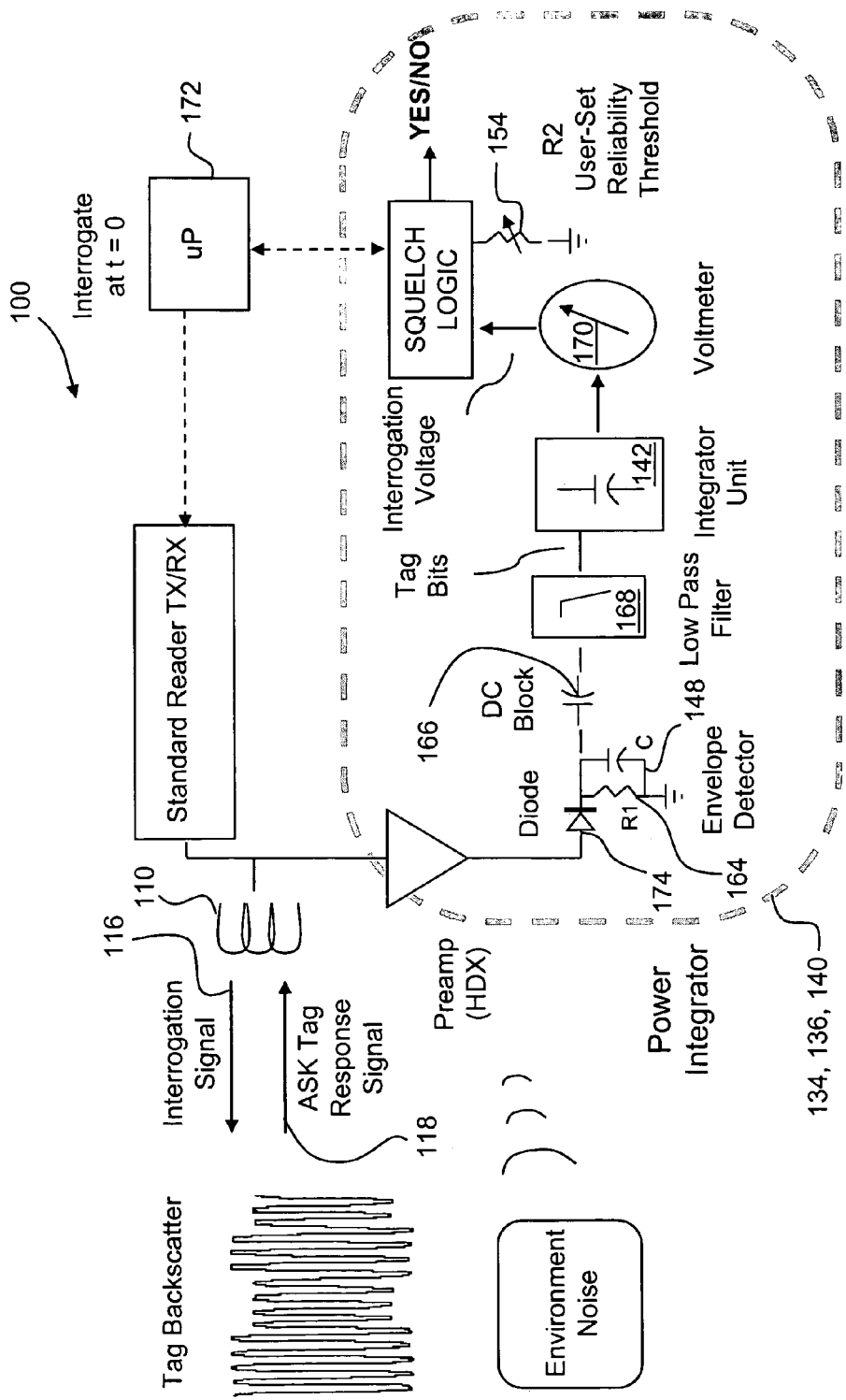
FIG. 12a is a schematic diagram of the power integrator in further detail.
Figures 12B, 12C:
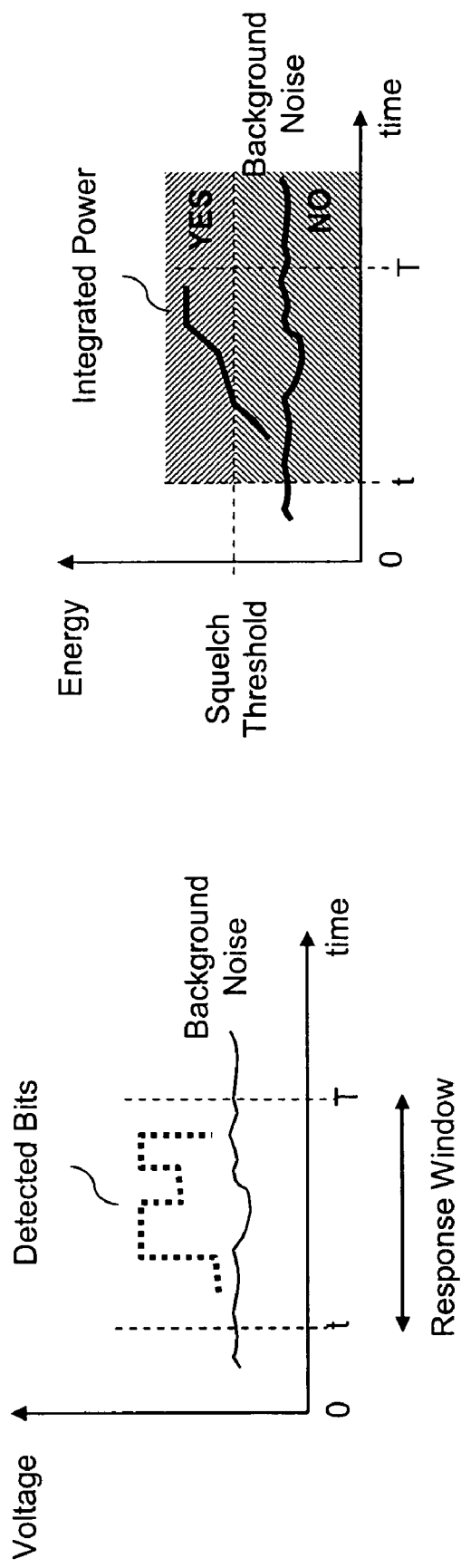
FIG. 12b is a graph of voltage versus time showing a plot of the detected bits contained within the RFID tag signals during the predetermined response time period and illustrating a plot of the environmental noise level measurement (i.e., background noise) during the same predetermined response time period.
FIG. 12c is a graph of energy versus time and illustrating a plot of power of the RFID tags integrated over time during the predetermined response time period and further illustrating a squelch threshold above which reliable detection of RFID tags may occur.

Referring now to FIGS. 12a-12c, shown is a schematic illustration of a preferred embodiment of the power integrator 140 which shares some of the same components for the bit counter 156 as described above, at least in the initial processing stages. The power integrator 140 sums up, either with a capacitor 148, operational amplifier 150, or using digital techniques well known in the art, the base band signal bits during the predetermined response time period (i.e., the response window-typically is 20 mS). The power integrator 140 then creates the highest possible voltage therefrom. A voltmeter 170 may be included in the power integrator 140 in order to measure the strength of the integrated signal and send such signal to the comparator 144 circuit in the squelch logic.

In the manner similar to that described above for the bit counter 156, the squelch logic establishes the threshold above which reliable detection of an RFID tag 112 may occur. Typically, 6 dB would be a sufficient margin over the quiet time environmental noise level measurement. An adjustable squelch via a switch, thumbwheel or programming may again be utilized to allow user augmentation of the squelch setting in order to adjust the false positives "reading" versus detection range. Indication of an RFID tag 112 occurs if the integrated power exceeds the squelch adjusted environmental noise level based upon quiet time measurement.

A further embodiment of the detector system 100 may be provided wherein the detector system 100 further includes a message detector 158 along with the presence detector 108. The message detector 158 may be configured to detect the identification code transmitted by the RFID tags 112 upon "activation" by the detector system 100. The identification code may be useful in determining the identity of the item 102 to which the RFID tag 112 is attached (e.g., surgical implement 104 and/or surgical instrument). The message detector 158 may have a decoder 132 that is configured to generate a decoder 132 signal with the message detector 158 being operative to cause its display device 160 to display message data generally containing information regarding the identification code. The identification code may be comprised of generally uncorrupted message bits transmitted from at least one of the RFID tags 112. More specifically, the signal transmitted by the RFID tags 112 is generally in the form of de-modulated bits of data with the recovered bits being either non-corrupted or corrupted (i.e., the bits are not necessarily valid 1's or 0's).

When the presence detector 108 and message detector 158 are combined in a single remote unit, the detector system 100 may be described as a "3-state" system in that the detector system 100 may indicate data regarding the existence of at least one of the following three states during sweeping of the patient wound: (1) "non-presence of RFID tags 112", (2) "presence of at least one RFID tag 112", (3) "identification code of at least one of the RFID tags 112".

Figure 16A:
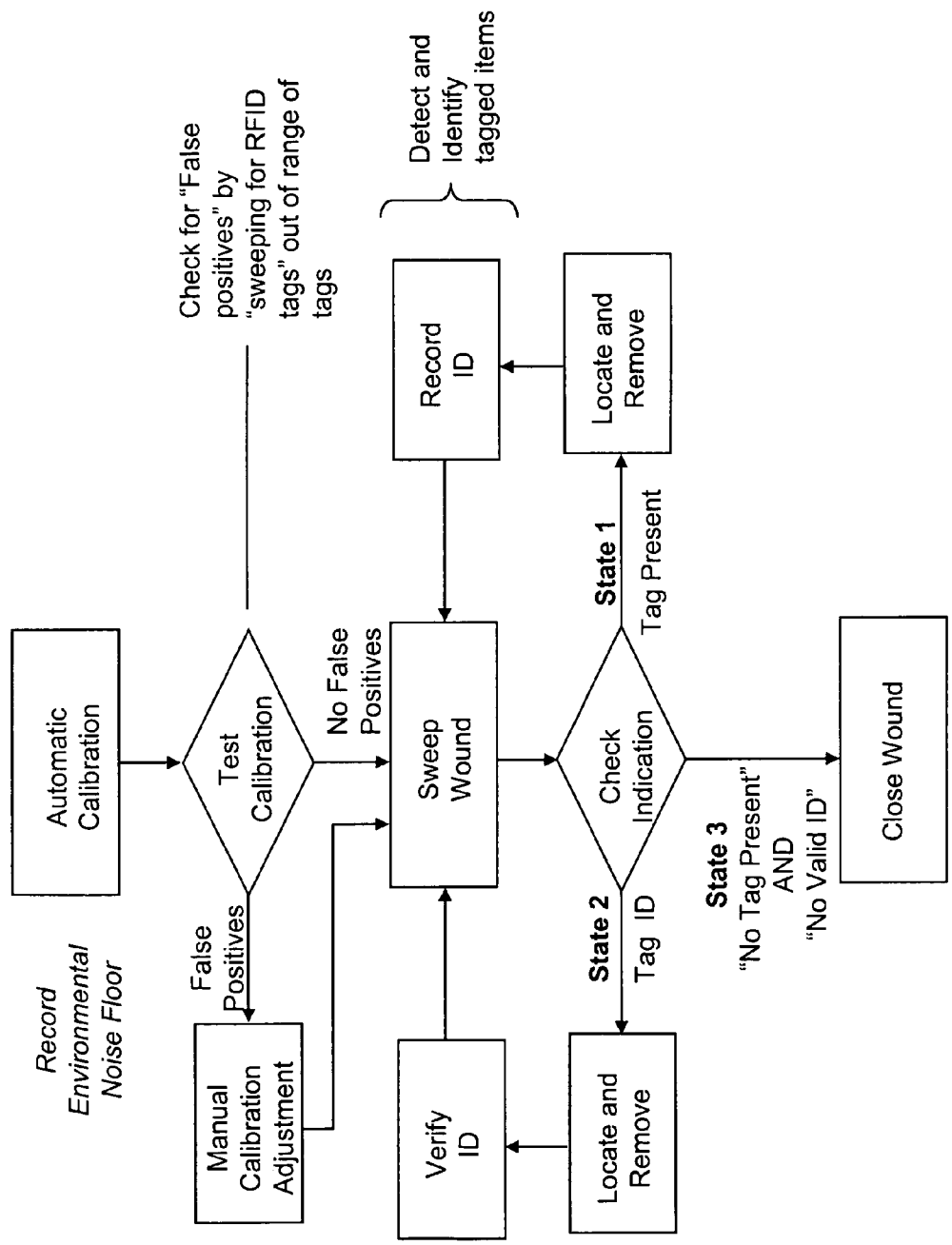
FIG. 16a is an algorithm by which the detector system may be utilized wherein the remote detector unit is first calibrated followed by adjustment of the squelch setting after which the patient wound may be swept for RFID tags and, if detected or identified, removed with the sequence being repeated until non-presence of any RFID tags is indicated.
Figure 16B:
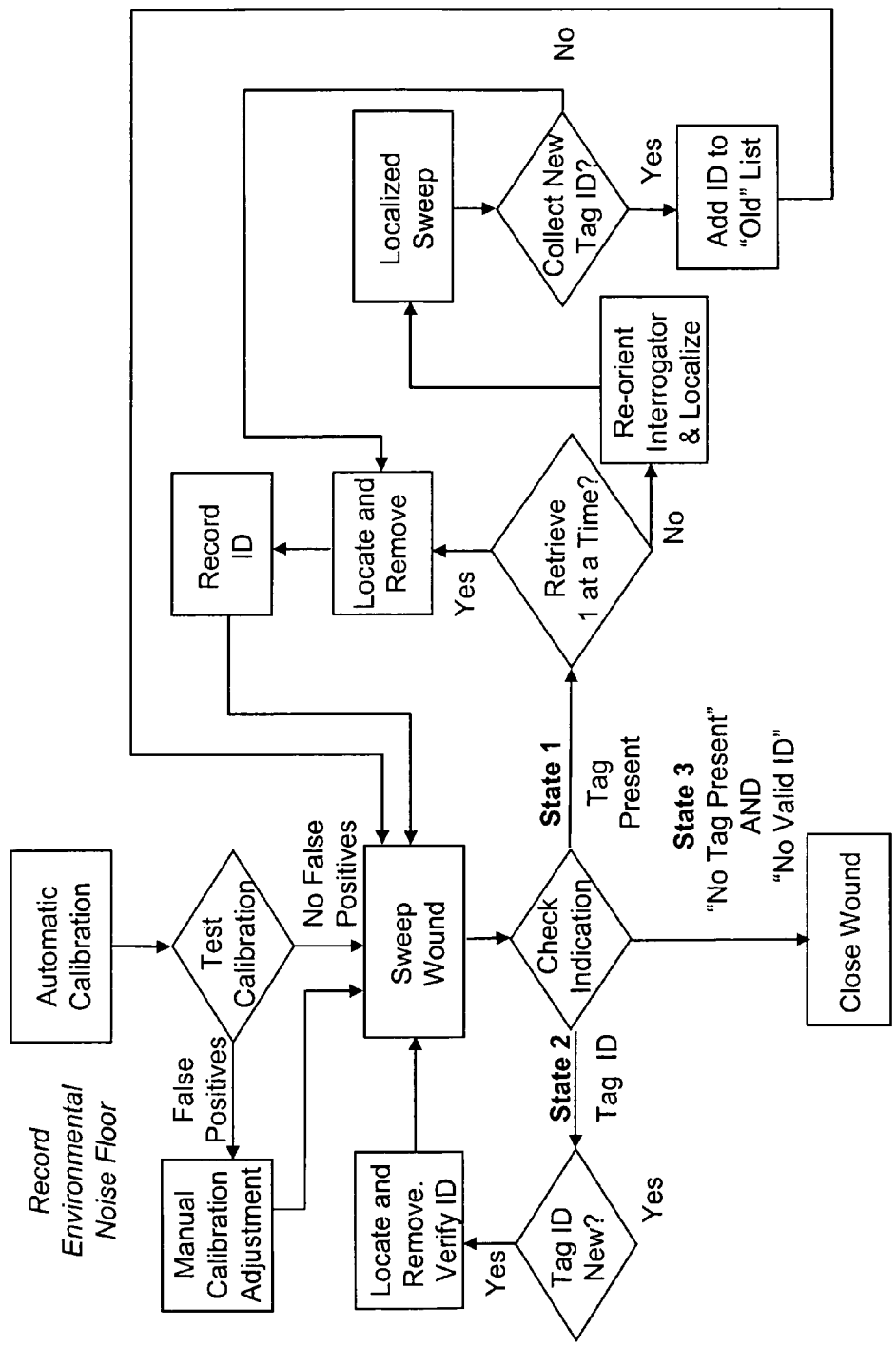
FIG. 16b is an algorithm by which presence and/or identification codes of the RFID tags may be determined in either sequential or simultaneous mode.
Figure 16C:
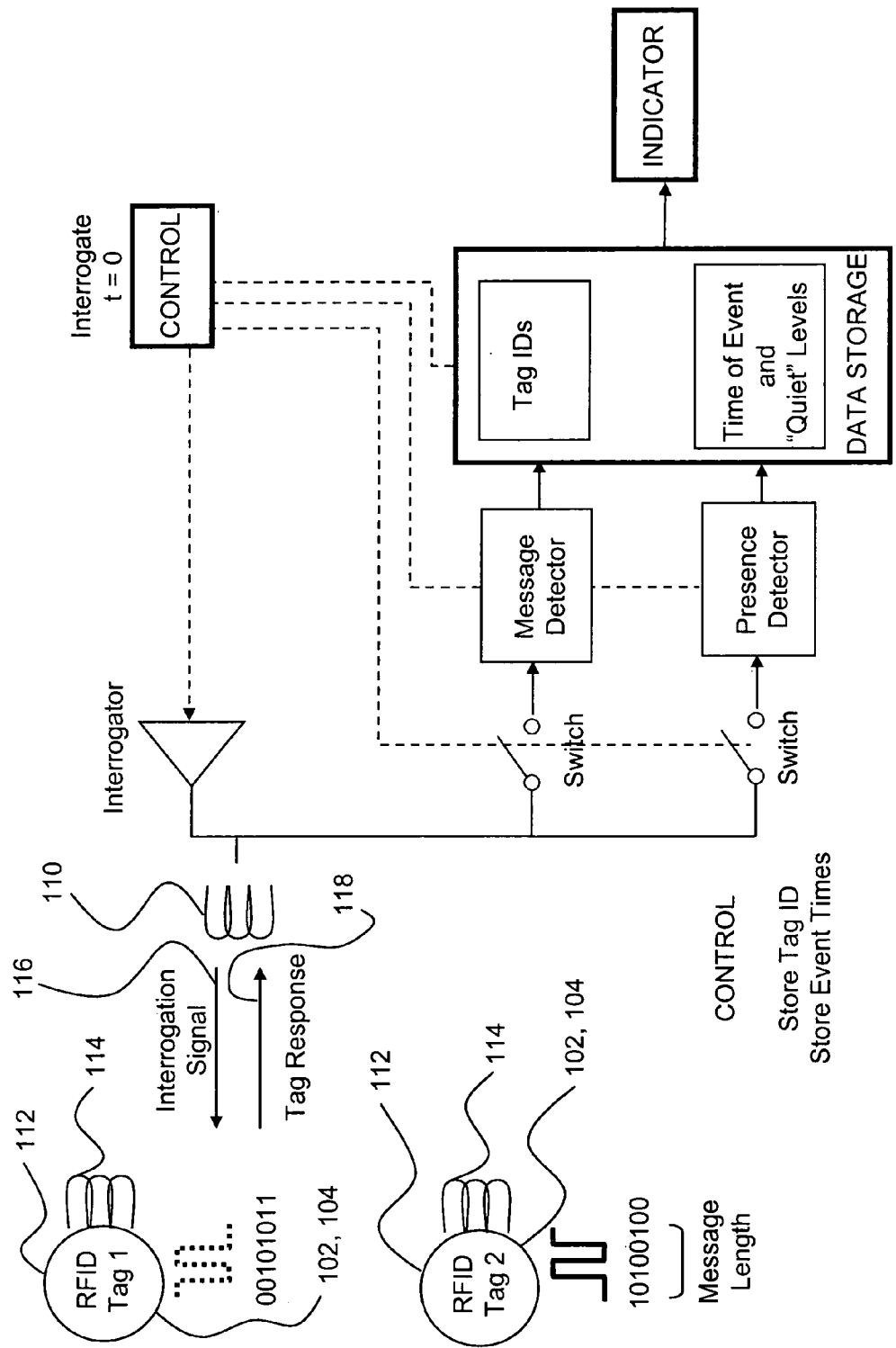
FIG. 16c is a circuit diagram wherein the remote detector unit comprises a presence and a message detector that are operative, in combination, to determine the existence of at least one of the following three states during the sweeping of the patient wound: non-presence of RFID tags, presence of at least one RFID tag, identification code of one of the RFID tags.

FIG. 16c illustrates the detector system 100 in the "3-state" embodiment and which is configured to store the identification codes of RFID tags 112 as well as store event times (i.e., RFID tag 112 detection times) as well as reference levels or environmental noise level or constellation pattern measurements. An indicator device 162 may be included with the "3-state" detector system 100 and may be configured as a display device 160 to provide visual readout of the identification code and/or presence or non-presence of RFID tags 112. Furthermore, the indicator device 162 may also be configured as an audible or vibratory apparatus or any combination thereof.

Referring to FIGS. 16a and 16b, shown is an algorithm for operation of a "3-state" detector system which may be configured to operate either sequentially, simultaneously, and/or any combination thereof (i.e., alternately). In general, such algorithms typically are initiated with a calibration procedure including measurement of the environmental noise level and or bit constellation measurement which may be accompanied by adjusting the squelch setting, if necessary. After calibration testing, the detector system is checked for a readout of "false positives" by "sweeping the remote detector" outside of the range of the RFID tags 112. Upon successful indication that "no false positives" are indicated, the operator may then sweep the wound with the combined presence and message detectors 108, 158 within range of the RFID tags 112. If RFID tags 112 are detected or identified, such items 102 to which the RFID tags 112 are secured may be located and removed from the patient wound. The operation is repeated until a reading of "non-presence of RFID tags 112" is displayed. Optionally, a reading of "no valid RFID tag 112" may also be displayed.

Figure 15A:
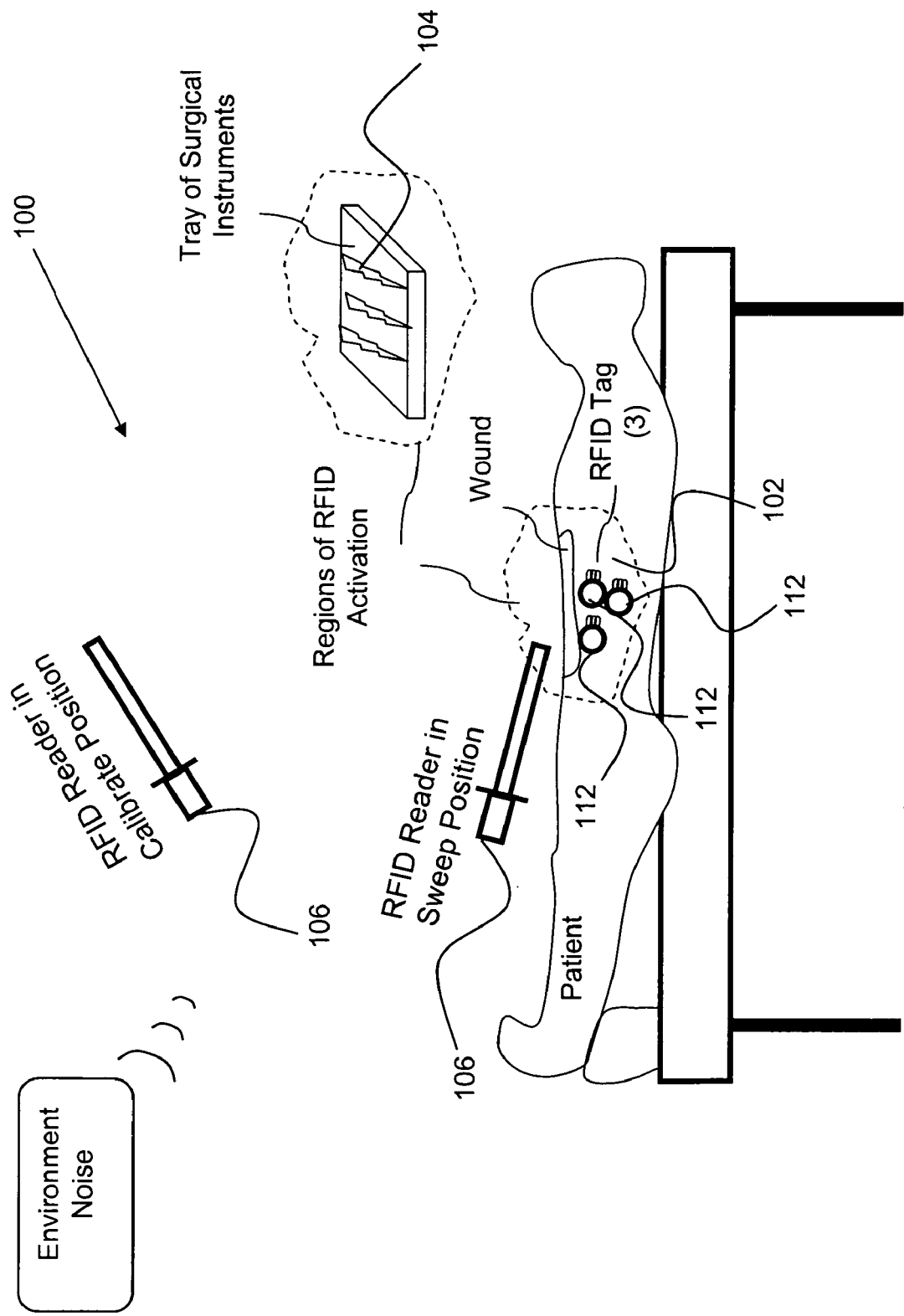
FIG. 15a illustrates implementation of the detector system in a surgical setting wherein the patient wound includes three RFID tags which may be attached to a corresponding number of surgical items and further illustrating selective positioning of the remote detector unit during a sweep to detect RFID tags and also illustrating a calibration position which is outside of the range within which the RFID tags are activatable.
Figure 15B:
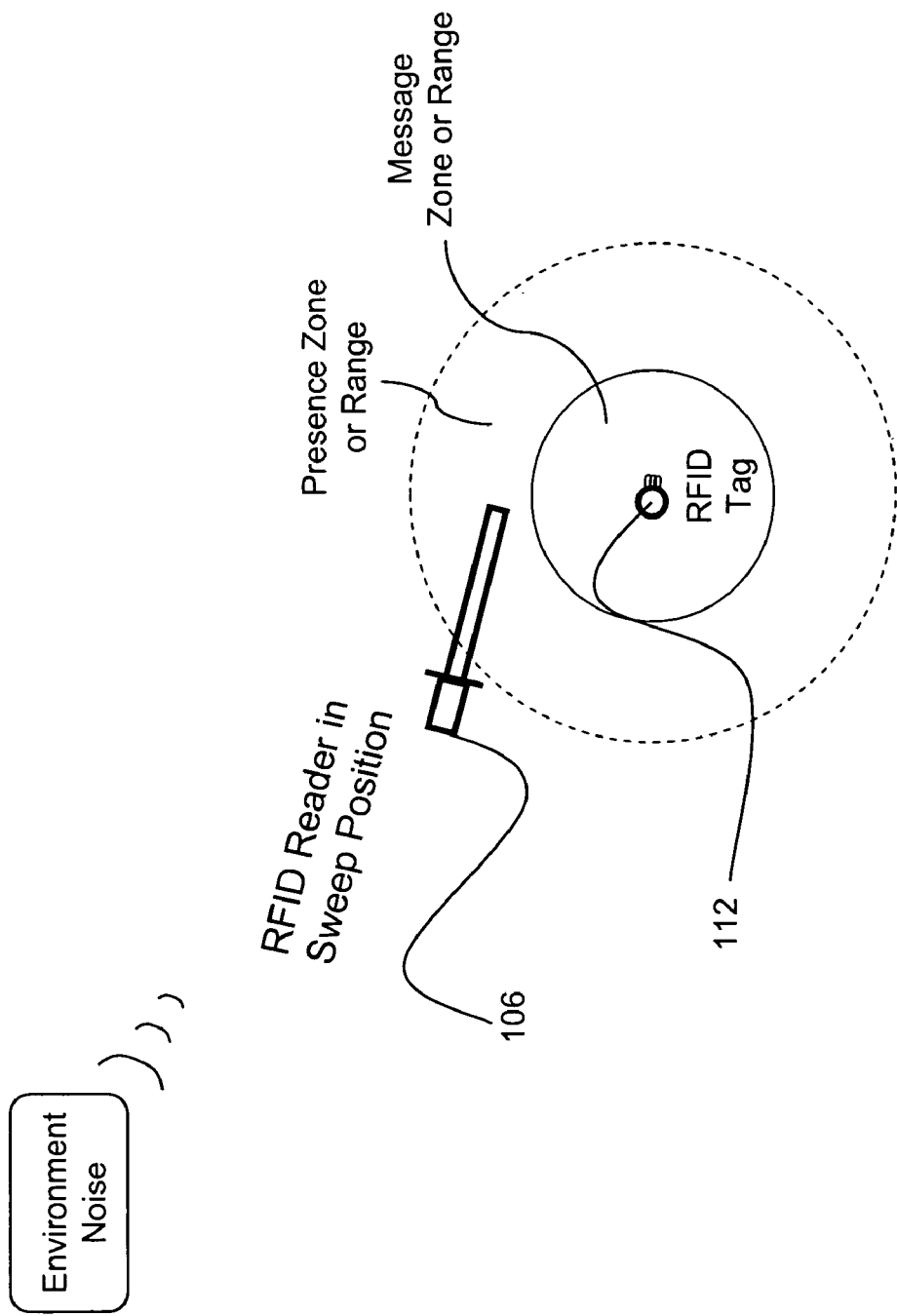
FIG. 15b is a schematic illustration of the remote detector unit which may be positioned within: a presence range wherein the presence of RFID tags may be detected, or, a message range within which the identification code(s) may be displayed by the remote detector unit.

As can be seen with reference to FIG. 15b, the presence detector 108 is operative to detect the presence of at least one of the RFID tags 112 within the presence range. However, the message detector 158 is operative to detect the identification code of at least one of the RFID tags 112 within a generally smaller message range. FIG. 16b represents an alternative algorithm by which the "3-state" detector system may be utilized. In this algorithm, an initial sweep for RFID tags 112 is performed and to approximately locate the surgical items 102 prior to moving tissues for removal of the surgical items 102 within the patient wound. In this manner, undue bleeding is avoided as well as a reduction in the risk of harm to internal organs. Following this initial sweep, the presence and message detectors 108, 158 may be re-oriented in order to gather an identification code reading from the RFID tags 112. Such readings are sequentially added to a list followed by continued sweep of the patient wound to look for additional RFID tags 112 while accumulating as many RFID tags 112 on the list as possible before commencing removal of the items 102.

Figure 17:
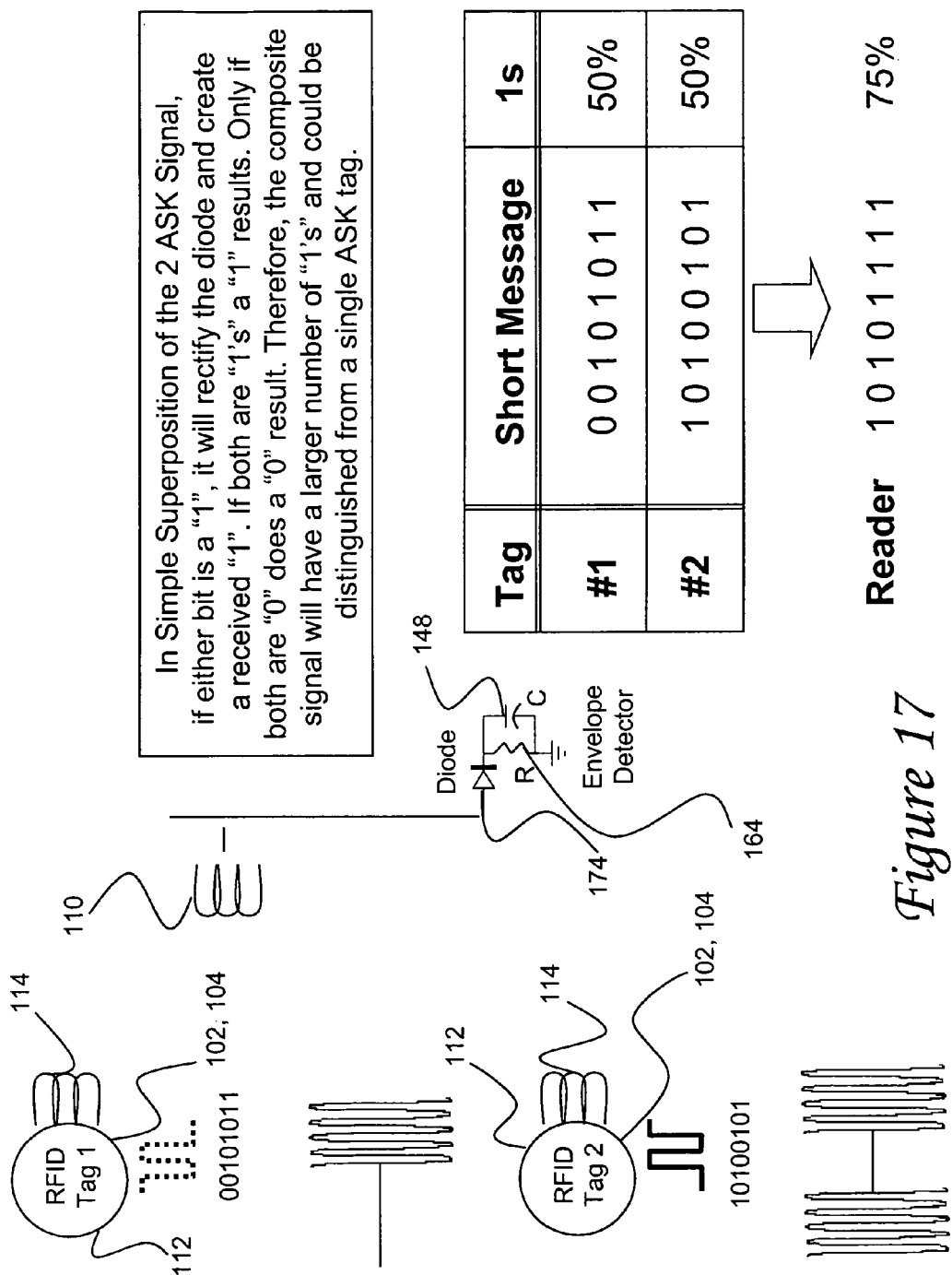
FIG. 17 is a schematic diagram of the bit counter that may be included with the constellation discriminator and which is shown with two RFID tags transmitting (amplitude shift keying) ASK and illustrating a principal by which the bit counter operates wherein, for example, 1's contained within the signal are summed in a composite signal which may be distinguished from environmental noise in order to indicate the presence of multiple RFID tags.

Referring briefly to FIG. 17, shown is a schematic diagram and table demonstrating an application where a bit counter 156 embodiment of the constellation discriminator 146 may successfully operate. The schematic diagram of FIG. 17 illustrates the detector system 100 with two RFID tags 112 that are ASK modulated. A change in bit pattern results in an increase in the percentage of 1's that may be recovered by the presence detector 108. This bit pattern change allows the detector system 100 to discriminate environmental noise from RFID tags 112 having colliding signals. In the example shown, the two RFID tags 112 transmit signals containing 50 percent 1's which results in a combined message containing 75 percent 1's as shown in the table. This resultant can then be distinguished against an environmental noise level (i.e., background noise) which on average contains 50 percent 1's.

Referring briefly to FIG. 18, shown is a table comparing the responses of a conventional or prior art RFID detector system compared to the same system having "anti-collision" technology and compared to the improved detector system 100 of the present invention. In the table, a checkmark indicates a positive response of the system to the various types of RFID tag configurations present (e.g., "2 or more Tags in Possible Contention", or, "0 Tags Present") under which each of three different types of interrogators can reliably perform. The negative responses in the bottom row of the table indicate that with any of the three systems, a negative response will mean "no tags" are present. As shown in the table, neither the prior art "RFID STANDARD READER" nor the prior art "RFID WITH ANTI-COLLISION SYSTEM" can reliably detect "1 or more Tags at Extended Distances." However, as shown in FIG. 18, the "RFID MULTI-TAG DETECTOR" (i.e., the detector system 100 of the present invention) can reliably detect "1 or more Tags at Extended Distances." As can be seen in FIG. 18, the improved detector system 100 advantageously provides a means for the five (5) possible RFID tag 112 scenarios while avoiding the cost of implementing "data collision" technology. In the improved detector system 100, no additional sophistication or additional technology is incorporated into the RFID tags 112. All the cost of the detector system 100 is incorporated into the presence and message detectors 108, 158 themselves and which are relatively low volumes compared to the number of RFID tags 112 that may be required in any given application (i.e., in a hospital setting).

The RFID tag 112 may be secured to any item 102 and is intended to be secured to surgical implements 104 and/or instruments which may be of either metallic and/or non-metallic construction or any combination thereof. Such instruments may include gauze pad, sponge, forceps, hemostats, clamps and or any items 102 typically used in an operating room. Furthermore, the detector system 100 is not limited to a specific modulation type but may be operative to receive modulated carrier frequencies from the RFID tags 112 using pulse shift modulation, frequency shift modulation, and amplitude shift modulation and/or any combination thereof.

In the preferred embodiment of the detector system 100, the "3-state" detector system 100 may be advantageously employed by incorporating the message and presence detectors 108 in a single remote unit that may be operated simultaneously. It should also be noted that although the above-described embodiments are typically targeted for a carrier frequency of about 125-134 kHz, the detector system 100 may be configured to operate in any frequency range of from about 30 kHz to about 3 GHz. For example, the detector system 100 may be configured to operate at 13.56 MHz, 900 MHz and 2.45 GHZ or any other suitable operating frequency.

Figure 19:
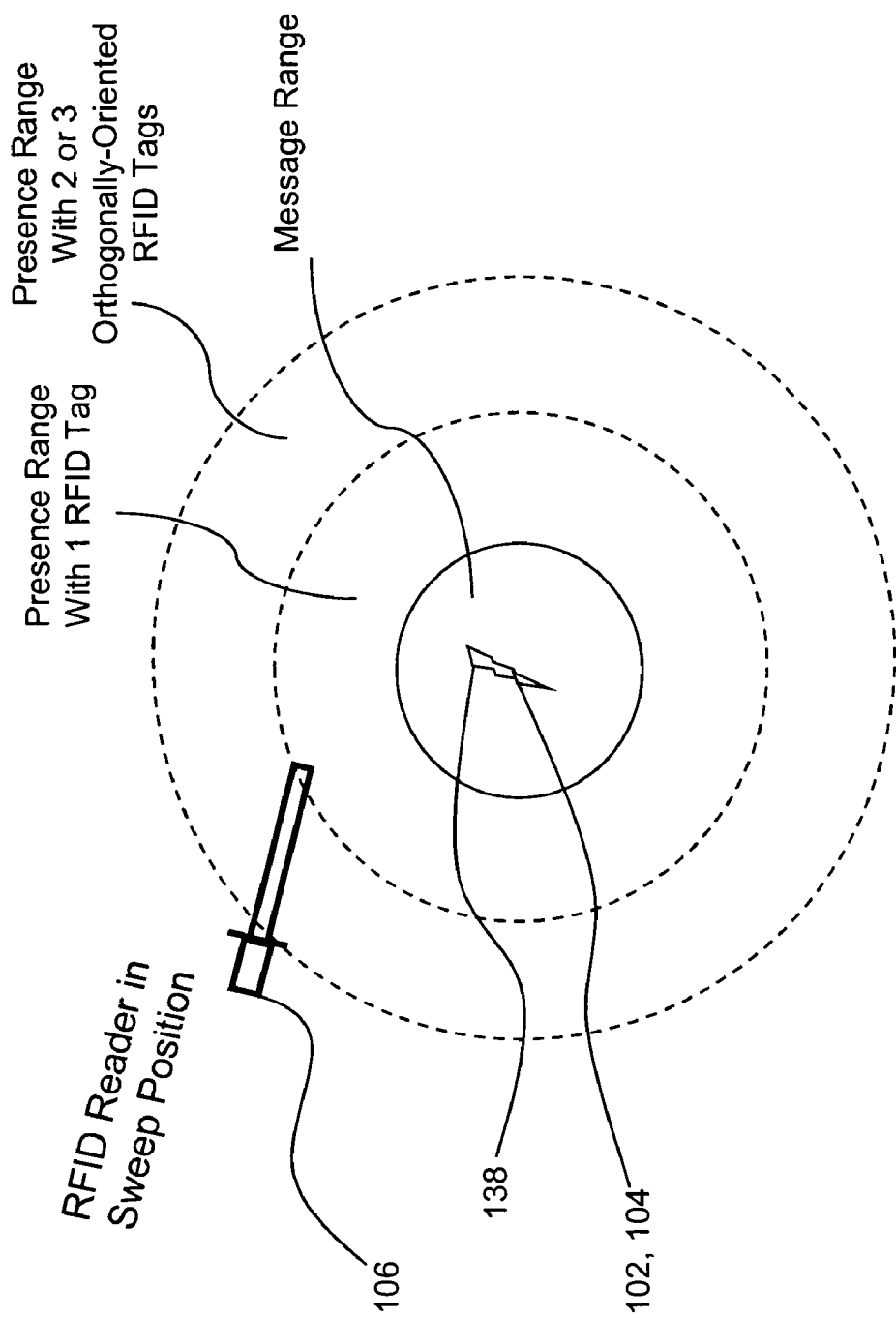
FIG. 19 is a schematic diagram showing the remote detector unit positioned within a presence range of a single surgical item having a tag assembly secured thereto and comprising 2 or 3 orthogonally-oriented RFID tags, or, the remote detector unit being positioned within a presence range for detecting a single surgical item having a single RFID tag, or, the remote detector unit being positioned within a message range for determining an identification code of an RFID tag.

Referring to FIG. 19, shown is an enhancement to the detector system 100 wherein instead of having a single RFID tag 112 secured thereto, each item 102 has a tag assembly 138 comprising 2 or 3 orthogonally-oriented RFID tags 112. The use of a tag assembly 138 results in an increase in the presence detection range beyond that which is available using a single RFID tag 112 (i.e., singly-tagged). In such an arrangement employing tag assemblies 138, the range over which the presence of an item 102 may be detected is greater than the presence range of a singly-tagged item. Furthermore, the range for detecting the presence of an item 102 with a single RFID tag 112 is greater than the range for determining the identification code for the same item 102.

In a singly-tagged arrangement, the orientation of remote detector unit 106 and RFID tag 112 antenna coils is typically 45° which results in a signal loss of cosine(45°)=0.71 loss or about 3 dB loss. This can be compared to an ideal orientation wherein the interrogating antenna 110 of the remote detector unit 106 and RF antenna 114 of the RFID tag 112 are aligned with one another. However, by attaching the tag assembly 138 comprising 3 of the RFID tags 112 to each item 102 with the RFID tags 112 being oriented orthogonally relative to one another, the 3 dB loss may be recovered. In other words, by including at least 2 and up to 3 RFID tags 112 on each item, it is more likely that that antenna coil of the remote detector unit 106 will be aligned nearly perfectly with at least one of the 3 RFID tags 112. The typical misalignment between the antennae coils of the remote detector unit 106 and the RFID tags 112 will likely be much less than 45°.

By employing tag assemblies 138, the range for detecting presence may be increased by 25-40% in association with a general decrease in signal propagation proportional to the square or cube of the distance between the remote detector unit 106 and the RFID tags 112. In a surgical sweep then, the presence of a multiply-tagged item 102 may be detected and then the item 102 may either be removed from the patient or the orientation of the remote detector unit 106 may be altered in order to acquire an un-collided identification code from one of the 2 or 3 RFID tags 112 in the tag assembly 138 that is attached to each item 102.

Because each item 102 now includes 2 or 3 RFID tags 112, some interference may be created for certain interrogation distances and orientations. However, the remote detector unit 106 can then be manipulated to a different distance and orientation which results in activation of only one RFID tag 112 thus allowing the retrieval of its associated identification code. In order to acquire singular association between the multiple RFID tags 112 and the detected item 102, it may be necessary either for all of the RFID tags 112 of the tag assembly 138 on each item 102 to have the same identification code, or, for the 2 or 3 RFID tags 112 of each tag assembly 138 to be correlated with the particular surgical item 102 such as via a hospital database.

Figure 20:
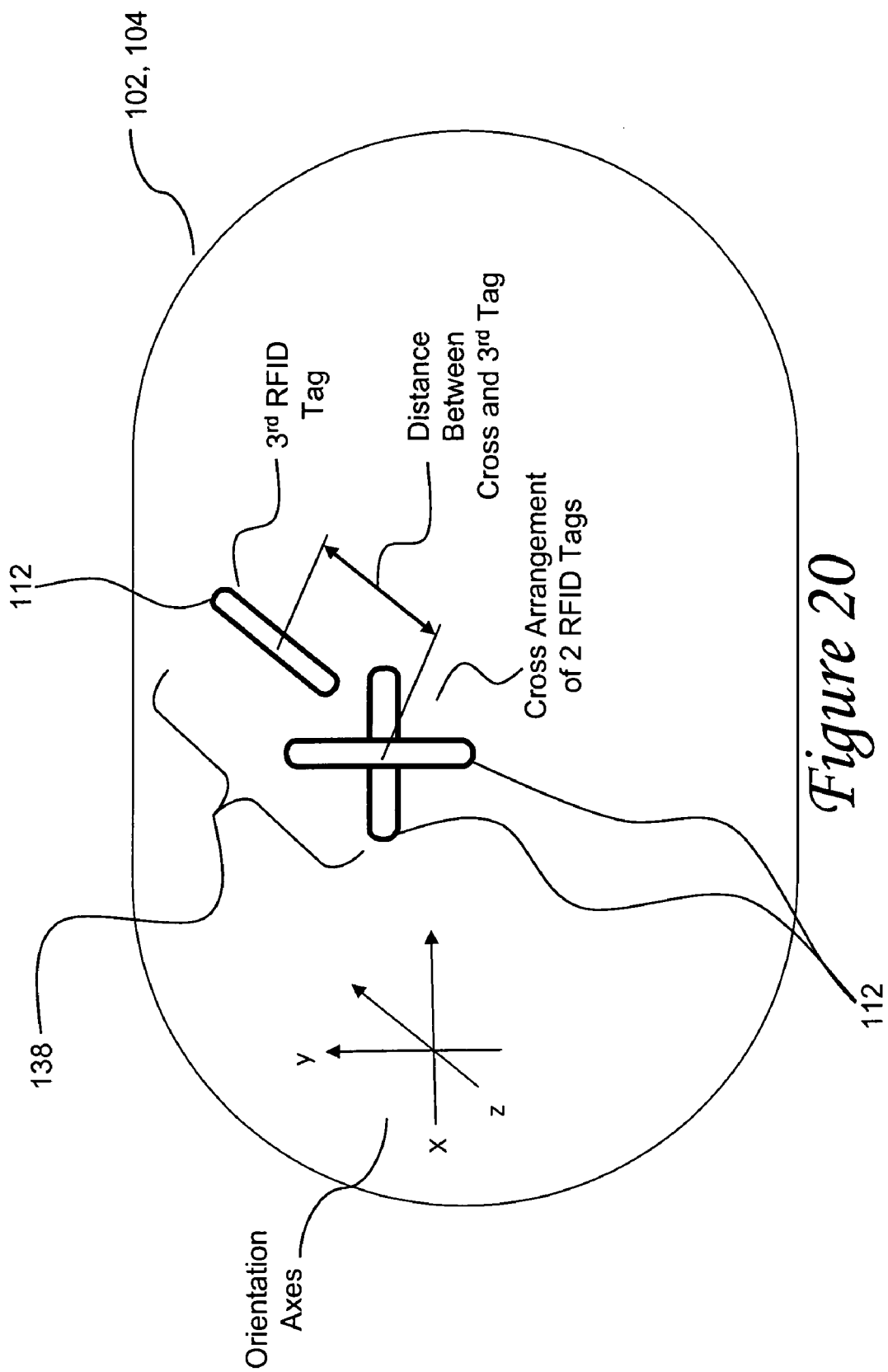
FIG. 20 is a schematic illustration of a surgical item to which may be attached the tag assembly comprising 2 or 3 RFID tags each oriented orthogonally (90°) relative to one another within three-dimensional space.

Referring to FIG. 20, shown is a surgical item 102 such as a sponge equipped with the tag assembly 138 having 2 or 3 RFID tags 112 oriented orthogonally relative to one another. In a two-RFID tag 112 arrangement of the tag assembly 138, the RFID tags 112 may be arranged in a "cross" formation relative to each other and generally defining a plane. It is believed that such a cross formation results only in a modest increase in overall RFID tag 112 thickness. In a three-RFID tag 112 arrangement of the tag assembly 138, in order to avoid adding unwanted bulk to the item, it may be necessary to find orthogonally-oriented surfaces on the item 102 which permits a planar and cross-plane attachment of RFID tags 112 to the item 102 without creating a gross increase in thickness or bulk of the item 102. It should be noted that in order for the tag assembly 138 with the three-RFID tag 112 arrangement to be effective, the distance between the RFID tags 112 in each tag assembly 138 is preferably substantially less than the interrogation distance in order to provide the greatest increase in detection range.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A detector system for detecting an RFID tag having an RF antenna and being configured to transmit therefrom a signal containing a modulated carrier frequency impressed with an identification code, the detector system comprising:
   a presence detector having an interrogating antenna configured to transmit a carrier frequency; and
   wherein:
      the RF and interrogating antennae are coupleable to one another within a presence range;
      the RFID tag being configured to transmit a signal in response to the carrier frequency received from the interrogating antenna;
      the interrogating antenna being configured to receive a signal from at least one of the following: the signal transmitted by the RFID tag, signals transmitted by a combination of environmental noise and the RFID tag;
   the presence detector further including:
      a signal reader configured to receive the modulated carrier frequency from the RFID tag during a predetermined response time period for comparison to a reference level for determining the presence of the RFID tag within the presence range.

2. The detector system of claim 1 wherein the signal reader is configured as a power integrator comprising:
   an integrator unit configured to receive the modulated carrier frequency during the predetermined response time period and sum power contained therein by integration; and
   a comparator connected to the integrator unit and configured to compare integrated signal power to the reference level; and
   wherein:
      the signals received by the integrator unit are one of the following: a detected voltage corresponding to the carrier frequency, demodulated bits corresponding to a composite of RFID transmission bits;
      the presence detector being configured to detect the presence of the RFID tag when the integrated signal power is greater than the reference level.

3. The detector system of claim 1 wherein the signal reader is configured as a constellation discriminator comprising:
   a demodulator configured to remove the carrier from the signal and recover a modulating message contained therewithin; and
   a comparator connected to the demodulator and being operative to receive bits contained in the modulating message during the predetermined response time period and compare a pattern of the bits to a predetermined reference constellation;
   wherein:
      the bits received by the constellation discriminator are comprised of one of the following: uncorrupted bits transmitted by the RFID tag, corrupted bits transmitted by a combination of environmental noise and the RFID tag;
      the presence detector being configured to detect the presence of the RFID tag when the bit pattern is distinguished from the reference constellation.

4. A detector system for detecting at least two RFID tags each having an RF antenna and being configured to transmit therefrom a signal containing a modulated carrier frequency impressed with an identification code, the detector system comprising:
   a presence detector having an interrogating antenna configured to transmit a carrier frequency; and
   wherein:
      the RF and interrogating antennae are coupleable to one another within a presence range;
      each one of the RFID tags being configured to transmit signals in response to the carrier frequency received from the interrogating antenna;
      the interrogating antenna being configured to receive signals from at least one of the following: signals transmitted by at least one of the RFID tags, signals transmitted by a combination of environmental noise and at least one of the RFID tags;
   the presence detector further including:
      a signal reader configured to receive the modulated carrier frequencies from the RFID tags during a predetermined response time period for comparison to a reference level for determining the presence of RFID tags within the presence range.

5. The detector system of claim 4 wherein the signal reader is configured as a power integrator comprising:
   an integrator unit configured to receive the modulated carrier frequencies during the predetermined response time period and sum power contained in the signals by integration thereof; and
   a comparator connected to the integrator unit and configured to compare integrated signal power to the reference level; and
   wherein:
      the signals received by the integrator unit are one of the following: a detected voltage corresponding to the carrier frequency, demodulated bits corresponding to a composite of RFID transmission bits;

the presence detector being configured to detect the presence of RFID tags when the integrated signal power is greater than the reference level.

6. The detector system of claim 5 wherein:
the presence detector further includes a front end circuit comprising a signal detector for detecting the modulated carrier frequencies in the signals;
the front end circuit including a demodulator configured to remove the carrier from the signals and recover modulating messages contained therewithin.

7. The detector system of claim 5 wherein the integrator unit includes at least one of the following for summing the power contained in the signals: a capacitor, an operational amplifier, a sampling circuit.

8. The detector system of claim 5 wherein:
the presence detector further includes an adjustable squelch circuit configured to allow for selection of a squelch setting;
the squelch setting being the point above the environmental noise level at which comparison thereof to the integrated signal power occurs.

9. The detector system of claim 4 wherein the signal reader is configured as a constellation discriminator comprising:
a demodulator configured to remove the carrier from the signals and recover a modulating message contained therewithin; and
a comparator connected to the demodulator and being operative to receive bits contained in the modulating message during the predetermined response time period and compare a pattern of the bits to a predetermined reference constellation;
wherein:
the bits received by the constellation discriminator are comprised of one of the following: uncorrupted bits transmitted by at least one of the RFID tags, corrupted bits transmitted by a combination of environmental noise and at least one of the RFID tags;
the presence detector being configured to detect the presence of RFID tags when the bit pattern is distinguished from the reference constellation.

10. The detector system of claim 9 wherein:
the constellation discriminator is configured as a bit counter configured to record a ratio of 1's to 0's in the bit pattern;
a nominal ratio of the bit pattern containing an equal proportion of 1's and 0's;
the bit counter being operative to determine the bit pattern type by comparing the nominal ratio to the ratio of the bit pattern received from the comparator.

11. The detector system of claim 9 wherein:
the presence detector further includes an adjustable squelch circuit configured to allow for selection of a squelch setting;
the squelch setting being the point above the environmental bit pattern at which comparison to the bit pattern occurs.

12. The detector system of claim 11 wherein the squelch setting is determined by a calibration procedure wherein the squelch is adjusted to a signal offset level corresponding to reliability of presence detection.

13. The detector system of claim 4 wherein the reference level is an environmental noise level measurement taken during a quiet period.

14. The detector system of claim 13 wherein the quiet period occurs during at least one of half-duplex and full-duplex operation while the RF antennae and the interrogating antenna are in at least one of the following states: non-transmitting, outside of the presence range.

15. The detector system of claim 4 wherein the presence detector further includes an indicator device connected to the signal reader and being configured to indicate the presence of RFID tags.

16. The detector system of claim 4 wherein the detector system further comprises a message detector and a display device, the message detector having a decoder configured to generate a decoder signal and being operative to cause the display device to display message data generally containing the identification code of generally uncorrupted message bits transmitted from at least one of the RFID tags.

17. The detector system of claim 16 wherein the presence and message detectors are operative to cause at least one of the display and indicator devices to indicate and display data relating to the existence of at least one of the following three states: non-presence of RFID tags, presence of at least one RFID tag, identification code of at least one of the RFID tags.

18. The detector system of claim 17 where the presence and message detectors are configured to operate in at least one of the following modes: sequentially, simultaneously.

19. The detector system of claim 4 wherein the integrated circuit is operative to modulate the carrier frequency using at least one of pulse shift modulation, frequency shift modulation, and amplitude shift modulation.

20. The detector system of claim 4 wherein at least one of the RFID tags is secured to a surgical implement.

21. The detector system of claim 4 wherein:
each of the at least two RFID tags comprises a tag assembly;
each tag assembly including at least two of the RFID tags oriented orthogonally relative to one another;
the RFID tags in each of the tag assemblies being disposed at a distance no greater than the presence range for a single one of the RFID tags.

22. A detector system for detecting a plurality of items each having at least one RFID tag secured thereto, each one of the RFID tags being operative to transmit an identification code, the detector system comprising:
a presence detector operative to detect the presence of at least one of the RFID tags within a presence range between the presence detector and the RFID tags;
a message detector operative to detect the identification code of at least one of the RFID tags within a message range between the presence detector and the RFID tags; and
an indicator device connected to the presence and message detectors;
wherein the presence and message detectors are operative to cause the indicator device to indicate the existence of at least one of the following three states: non-presence of RFID tags, presence of at least one RFID tag, identification code of at least one of the RFID tags.

23. The detector system of claim 22 wherein:
each item has a tag assembly secured thereto;
each tag assembly including at least two of the RFID tags oriented orthogonally relative to one another;
the RFID tags in each of the tag assemblies being disposed at a distance no greater than the presence range for a single one of the RFID tags.

24. A method for detecting a plurality of items each having an RFID tag secured thereto, the method comprising the steps of:
a. establishing a reference level during a quiet period;
b. transmitting a carrier frequency from a presence detector;
c. receiving the carrier frequency at the RFID tags located within a presence range of the presence detector;

d. impressing an identification code of each of the RFID tags onto a plurality of the carrier frequencies by modulation thereof;

e. transmitting the modulated carrier frequencies from the RFID tags to the presence detector;

f. receiving at the presence detector during a predetermined response time period a composite signal comprised of at least one of the following: signals transmitted by at least one of the RFID tags, signals transmitted by a combination of environmental noise and at least one of the RFID tags;

g. comparing the composite signal to the reference level; and h. generating a comparator signal when the composite signal is distinguished from the reference level.

25. The method of claim 24 wherein the step (g) of comparing the composite signal to the reference level is comprised of:

1. summing power contained in the composite signal by integration thereof;
2. comparing the integrated signal power to the reference level; and
3. generating the comparator signal when the integrated signal power exceeds the reference level.

26. The method of claim 25 further comprising:

adjusting a squelch setting to regulate a point above the environmental noise level at which comparison thereof to the integrated signal power occurs.

27. The method of claim 24 further comprising:

indicating the presence of RFID tags in response to the comparator signal.

28. The method of claim 24 further comprising:

removing a carrier from the signals contained in the composite signal; and recovering a modulating message contained within the signals;

wherein:

the reference level is a predetermined reference constellation;

the step (g) of comparing the composite signal to the reference level being comprised of:

1. receiving bits contained in the modulating message during the predetermined response time period;
2. comparing a pattern of the bits to the reference constellation; and
3. generating the comparator signal when the bit pattern is distinguished from the reference constellation.

29. The method of claim 28 further comprising:

adjusting a squelch setting to regulate a point above an environmental bit pattern at which comparison to the bit pattern occurs.

30. The method of claim 24 wherein the carrier frequencies are modulated using at least one of pulse shift modulation, frequency shift modulation, and amplitude shift modulation.

31. The method of claim 24 wherein the reference level is an environmental noise level measurement taken during a quiet period.

32. The method of claim 31 wherein the quiet period occurs during at least one of half-duplex and full-duplex operation while the presence detector and RFID tags are in at least one of the following states: non-transmitting, outside of the presence range.

33. The method of claim 24 wherein the step of indicating the presence of RFID tags comprises displaying data regarding the RFID tags.

34. The method of claim 24 further comprising the step of detecting the identification code of generally uncorrupted message bits transmitted from at least one of the RFID tags.

35. The method of claim 34 further comprising the step of indicating and displaying data relating to the existence of at least one of the following three states: non-presence of RFID tags, presence of at least one of the RFID tags, identification code of at least one of the RFID tags.

36. The method of claim 24 wherein at least one of the RFID tags is secured to a surgical implement.

37. The method of claim 24 wherein:

each item has a tag assembly secured thereto;

each tag assembly including at least two of the RFID tags oriented orthogonally relative to one another;

the RFID tags in each of the tag assemblies being disposed at a distance no greater than the presence range for a single one of the RFID tags.

* * * * *